(12) United States Patent
Kim et al.

(10) Patent No.: US 9,775,537 B2
(45) Date of Patent: Oct. 3, 2017

(54) BIO SIGNAL MEASURING APPARATUS AND USER MONITORING SYSTEM INCLUDING THE SAME

(71) Applicant: Industry-Academic Cooperation Foundation, Yonsei University, Seoul (KR)

(72) Inventors: Tae Wook Kim, Seoul (KR); Honggul Han, Busan (KR)

(73) Assignee: Industry-Adademic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 14/710,971

(22) Filed: May 13, 2015

(65) Prior Publication Data
US 2015/0327774 A1   Nov. 19, 2015

(30) Foreign Application Priority Data

May 13, 2014   (KR) .......................... 10-2014-0057352
Jun. 23, 2014   (KR) .......................... 10-2014-0076488
Aug. 20, 2014   (KR) .......................... 10-2014-0108129

(51) Int. Cl.
*A61B 5/02* (2006.01)
*A61B 5/05* (2006.01)
(Continued)

(52) U.S. Cl.
CPC ............ *A61B 5/0507* (2013.01); *A61B 5/024* (2013.01); *A61B 5/1107* (2013.01);
(Continued)

(58) Field of Classification Search
CPC ...... A61B 5/024; A61B 5/6887; A61B 5/7278; A61B 5/0507; A61B 5/1107; A61B 5/6893
See application file for complete search history.

(56) References Cited

U.S. PATENT DOCUMENTS

2014/0163386 A1\* 6/2014 He ...................... A61B 5/7203
600/476

FOREIGN PATENT DOCUMENTS

JP   H10-504976   5/1998
JP   2003-126090   5/2003
(Continued)

OTHER PUBLICATIONS

Shin, J. Y., et al., A Study of Noncontact Heartbeat and Respiration Detection Using the Doppler Radar, The Institute of Electronics and Information Engineers, 2009-46SC-1-1, Jan. 2009, 9 pgs.
(Continued)

*Primary Examiner* — Niketa Patel
*Assistant Examiner* — Lindsey G Wehrheim
(74) *Attorney, Agent, or Firm* — Procopio, Cory, Hargreaves & Savitch LLP

(57) ABSTRACT

A bio signal measuring apparatus is provided which includes a sampling unit, and a processing unit. The sampling unit samples a portion of a pulse included in a pulse signal penetrating a person to be measured, and portions sampled from a plurality of pulses included in the pulse signal are different from each other. The processing unit processes a sampled signal and measures a bio signal of the person to be measured based on at least one of a center frequency, a bandwidth, or amplitude of a reconstruction pulse obtained through the sampling.

9 Claims, 21 Drawing Sheets

(51) Int. Cl.
*A61B 5/00* (2006.01)
*A61B 5/024* (2006.01)
*A61B 5/11* (2006.01)

(52) U.S. Cl.
CPC .......... *A61B 5/6887* (2013.01); *A61B 5/7278* (2013.01); *A61B 5/6893* (2013.01)

(56) References Cited

FOREIGN PATENT DOCUMENTS

| | | |
|---|---|---|
| JP | 2013-153783 | 8/2013 |
| KR | 10-0233488 | 9/1999 |
| KR | 10-0665567 | 12/2006 |
| KR | 10-2007-0120815 | 12/2007 |
| KR | 10-2009-0022085 | 3/2009 |
| KR | 10-0905102 | 6/2009 |
| KR | 10-2011-0105411 | 9/2011 |
| KR | 10-2013-0051992 | 5/2013 |
| KR | 10-2013-0124210 | 11/2013 |
| KR | 10-2014-0073348 | 6/2014 |

OTHER PUBLICATIONS

Wang, L., et al., 3-5 GHz 4-Channel UWB Beamforming Transmitter With 1° Scanning Resolution Through Calibrated Vernier Delay Line in 0.13-μm CMOS, IEEE Journal of Solid-State Circuits 47(12) Dec. 2012, pp. 3145-3159.
Notice of Allowance for KR App No. 10-2014-0108129 dated Nov. 16, 2015, 5 pgs.
Notice of Allowance for KR App No. 10-2014-0076488 dated Nov. 16, 2015, 5 pgs.
Notice of Allowance dated May 15, 2014, for Korean App No. 10-2014-0057352, 5 pgs.

\* cited by examiner

BIO SIGNAL MEASURING APPARATUS AND USER MONITORING SYSTEM INCLUDING THE SAME

CROSS-REFERENCE TO RELATED APPLICATIONS

A claim for priority under 35 U.S.C. §119 is made to Korean Patent Application Nos. 10-2014-0057352 filed on May 13, 2014; 10-2014-0076488 filed on Jun. 23, 2014; and 10-2014-0108129 filed on Aug. 20, 2014, in the Korean Intellectual Property Office, the entire contents of which are hereby incorporated by reference.

BACKGROUND

Embodiments of the inventive concepts described herein relate to a bio signal measuring apparatus and a user monitoring system including the same.

In general, a method for measuring electrocardiogram (ECG) with electrodes contacting to a body of a person to be measured may be used to check a heart condition. However, the method for measuring the ECG using electrodes may be inconvenient to use because the electrodes are in contact with the body.

A non-contact type heartbeat measuring method may be used to solve inconvenience to measure a heartbeat in a contact type. In the non-contact type heartbeat measuring method, the heartbeat may be measured using a reflected wave that is reflected from a body of a person to be measured after transmitting a wireless signal toward a heart of the patient.

However, the method using the reflected wave may have a disadvantage in that an error due to movement of the person to be measured is great because the heartbeat is measured based on a distance between a transceiver and a body.

SUMMARY

Embodiments of the inventive concepts provide a bio signal measuring apparatus and a user monitoring system including the same, capable of measuring a bio signal including a heartbeat without influence due to movement of a person to be measured.

Embodiments of the inventive concepts also provide a bio signal measuring apparatus and a user monitoring system including the same, capable of measuring a bio signal using hardware of low performance for processing a signal in a low speed and consuming less power.

One aspect of embodiments of the inventive concept is directed to provide a bio signal measuring apparatus is provided which includes a sampling unit, and a processing unit. The sampling unit samples a portion of a pulse included in a pulse signal penetrating a person to be measured, and portions sampled from a plurality of pulses included in the pulse signal are different from each other. The processing unit processes a sampled signal to measure a bio signal of the person to be measured based on at least one of a center frequency, a bandwidth, or amplitude of a reconstruction pulse obtained through the sampling.

The bio signal measuring apparatus may further include an antenna. The antenna receives a pulse signal penetrating the person to be measured and provides the pulse signal to the sampling unit.

The bio signal measuring apparatus may further include an analog-to-digital converter. The analog-to-digital converter converts a sampled signal into a digital signal and provides the digital signal to the processing unit.

The pulse signal may be a signal where the pulse is repeated every predetermined pulse repetition period.

Duration of the reconstruction pulse may be longer than that of the pulse.

The sampling unit may sample the pulse in at least one time of the duration of the pulse, and sampling about the pulse may be performed every time obtained by adding a predetermined sampling interval to the pulse repetition period.

The sampling unit may sample the pulse at a plurality of times of the duration of the pulse, and an interval between the times in the duration of the pulse may be equal to the sampling interval.

The processing unit may obtain an average of sampling values, corresponding to different points in the duration of the pulse, from among sampling values obtained by sampling the plurality of pulses and may determine the average as a sampling value of a corresponding point.

The processing unit may measure a heartbeat of the person to be measured, based on at least one of a center frequency, a bandwidth, or amplitude of the reconstruction pulse.

The processing unit may calculate a variation in at least one of a center frequency, a bandwidth, or amplitude of the reconstruction pulse and may measure the heartbeat by detecting contraction and distension of a heart according to the variation.

The processing unit may calculate at least one of a center frequency, a bandwidth, or amplitude of the reconstruction pulse and may measure the heartbeat by detecting contraction and distension of a heart according to at least one of the center frequency, the bandwidth, the amplitude.

Another aspect of embodiments of the inventive concept is directed to provide a user monitoring system which includes a transmitter configured to generate a pulse signal to transmit the pulse signal to a user and a bio signal measuring apparatus arranged to receive the pulse signal from the transmitter with the user interposed therebetween and configured to measure a bio signal of the user. The bio signal measuring apparatus is provided which includes a sampling unit, and a processing unit. The sampling unit samples a portion of a pulse included in the pulse signal penetrating the user, and portions sampled from a plurality of pulses included in the pulse signal are different from each other. The processing unit processes a sampled signal to measure a bio signal of the user based on at least one of a center frequency, a bandwidth, or amplitude of a reconstruction pulse obtained through the sampling.

The user monitoring system may further include an antenna. The antenna receives the pulse signal penetrating the user and provides the pulse signal to the sampling unit.

The user monitoring system may further include an analog-to-digital converter. The analog-to-digital converter converts a sampled signal into a digital signal and provides the digital signal to the processing unit.

The pulse signal may be a signal where the pulse is repeated every predetermined pulse repetition period.

Duration of the reconstruction pulse may be longer than that of the pulse.

The sampling unit may sample the pulse in at least one time of the duration of the pulse, and sampling about the pulse may be performed every time obtained by adding a predetermined sampling interval to the pulse repetition period.

The sampling unit may sample the pulse at a plurality of times of the duration of the pulse, and an interval between the times in the duration of the pulse may be equal to the sampling interval.

The processing unit may obtain an average of sampling values, corresponding to different points in the duration of the pulse, from among sampling values obtained by sampling the plurality of pulses and may determine the average as a sampling value of a corresponding point.

The processing unit may measure a heartbeat of the user based on at least one of a center frequency, a bandwidth, or amplitude of the reconstruction pulse.

The processing unit may calculate a variation in at least one of a center frequency, a bandwidth, or amplitude of the reconstruction pulse and may measure the heartbeat by detecting contraction and distension of a heart according to the variation.

The processing unit may calculate at least one of a center frequency, a bandwidth, or amplitude of the reconstruction pulse and may measure the heartbeat by detecting contraction and distension of a heart according to at least one of the center frequency, the bandwidth, the amplitude.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
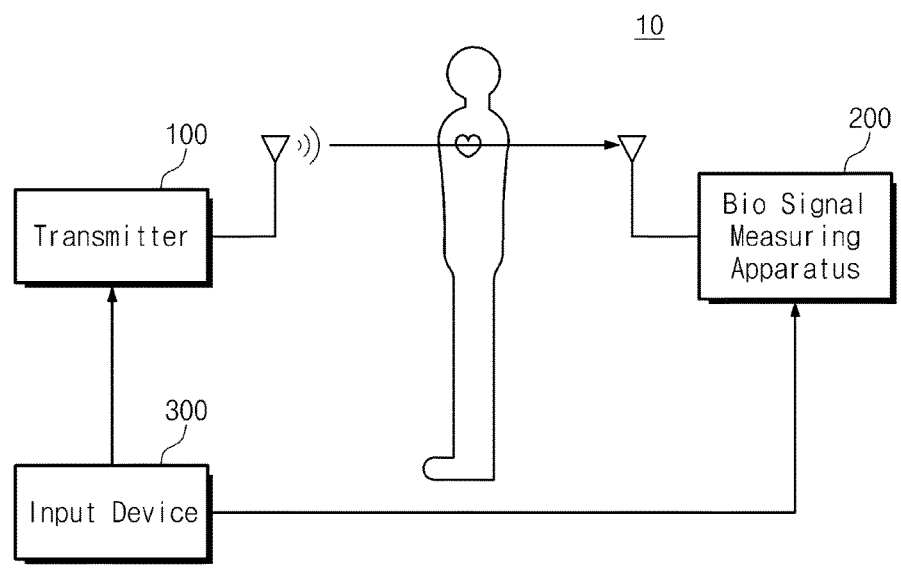
FIG. 1 is a block diagram schematically illustrating a user monitoring system according to an exemplary embodiment of the inventive concept.

Embodiments will be described in detail with reference to the accompanying drawings. The inventive concept, however, may be embodied in various different forms, and should not be construed as being limited only to the illustrated embodiments. Rather, these embodiments are provided as examples so that this disclosure will be thorough and complete, and will fully convey the concept of the inventive concept to those skilled in the art. Accordingly, known processes, elements, and techniques are not described with respect to some of the embodiments of the inventive concept. Unless otherwise noted, like reference numerals denote like elements throughout the attached drawings and written description, and thus descriptions will not be repeated. In the drawings, the sizes and relative sizes of layers and regions may be exaggerated for clarity.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the inventive concept.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Also, the term "exemplary" is intended to refer to an example or illustration.

It will be understood that when an element or layer is referred to as being "on", "connected to", "coupled to", or "adjacent to" another element or layer, it can be directly on, connected, coupled, or adjacent to the other element or layer, or intervening elements or layers may be present. In contrast, when an element is referred to as being "directly on," "directly connected to", "directly coupled to", or "immediately adjacent to" another element or layer, there are no intervening elements or layers present.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

In the description below, it will be understood that when an element such as a layer, region, substrate, plate, or member is referred to as being "on" another element, it can be directly on the other element or intervening elements may be present. In contrast, the term "directly" means that there are no intervening elements.

FIG. 1 is a block diagram schematically illustrating a user monitoring system 10 according to an exemplary embodiment of the inventive concept.

As illustrated in FIG. 1, a user monitoring system 10 may contain a transmitter 100 and a bio signal measuring apparatus 200.

The transmitter 100 may generate a pulse signal and may transmit the pulse signal to a user. The bio signal measuring apparatus 200 may be disposed to face the transmitter 100 with the user interposed therebetween.

According to an exemplary embodiment of the inventive concept, the bio signal measuring apparatus 200 may measure a bio signal of the user using a pulse signal that is emitted from the transmitter 100 and penetrates the user.

According to an exemplary embodiment of the inventive concept, the bio signal measuring apparatus 200 may measure a heartbeat using the bio signal of the user, but the measured bio signal may not be limited thereto. As will be described later, as the pulse signal penetrates the user, signal characteristics including a bandwidth may vary. In this case, the bio signal measuring apparatus 200 may measure a condition or movement of an internal organ of the user as well as a heart.

The user monitoring system 10 may measure a bio signal of the user and may monitor a condition of the user based on the measured bio signal.

In exemplary embodiments, the user monitoring system 10 may be installed at a vehicle to monitor conditions of a passenger as well as a driver, but an application field of the user monitoring system 10 may not be limited thereto.

For example, the user monitoring system 10 may be installed at a place (e.g., a cinema or theater) where movement of a user is less, thereby monitoring a condition of the audience.

Figure 2:
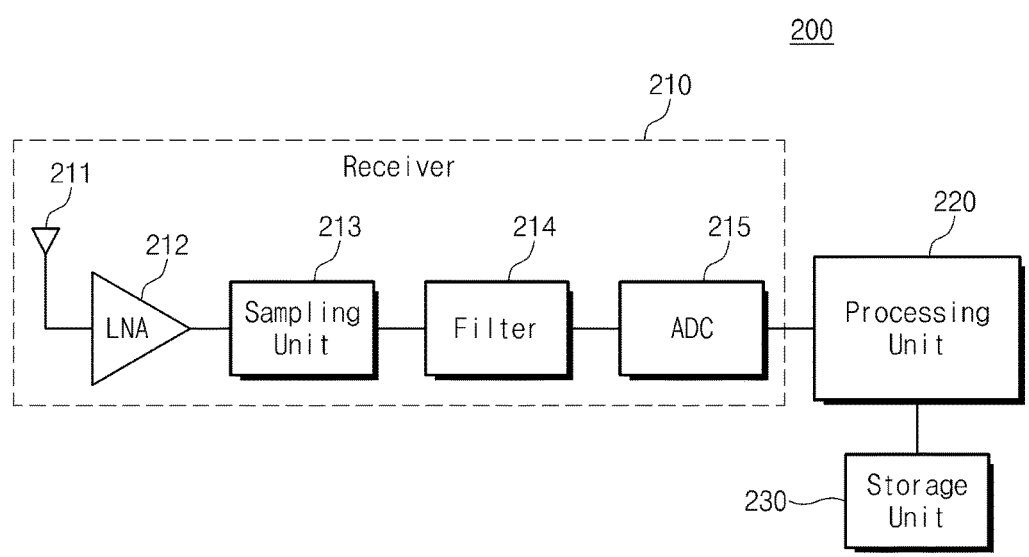
FIG. 2 is a block diagram schematically illustrating a bio signal measuring apparatus according to an exemplary embodiment of the inventive concept.

FIG. 2 is a block diagram schematically illustrating a bio signal measuring apparatus 200 according to an exemplary embodiment of the inventive concept.

As illustrated in FIG. 2, a bio signal measuring apparatus 200 may contain a receiver 210, a processing unit 220, and a storage unit 230.

The receiver 210 may receive a pulse signal that is emitted from a transmitter 100 and penetrates a person to be measured. The processing unit 220 may process the received pulse signal to analyze a bandwidth of the pulse signal and may measure a bio signal of the to-be-measured person based on a result of analyzing the bandwidth. The storage unit 230 may store data used to measure the bio signal.

In exemplary embodiments, the receiver 210 may contain an antenna 211, an amplifier 212, a sampling unit 213, and an analog-to-digital converter 215. The antenna 211 may receive a pulse signal that penetrates a user from which a bio signal is measured, that is, a person to be measured.

The amplifier 212 may amplify a received signal, and may be formed of, for example, a low noise amplifier. The sampling unit 213 may sample the amplified signal. The analog-to-digital converter 215 may convert the sampled signal into a digital signal. in exemplary embodiments, the a filter 214 may be further provided between the sampling unit 213 and the analog-to-digital converter 215 to remove unnecessary noise included in a signal at the sampling operation.

The processing unit 220 may process the digital signal to analyze a bandwidth of the pulse signal and may measure a bio signal of a to-be-measured person based on a result of analyzing the bio signal. The processing unit 220 may be a processor that calls and executes, the storage unit 230, a program used to measure a bio signal, and may include, for example, a central processing unit (CPU).

The storage unit 230 may be a storage device that stores a variety of data used to measure the bio signal and may include, for example, a register, a RAM, a ROM, a hard disk drive (HDD), a solid state drive (SSD), and the like.

Figure 3:
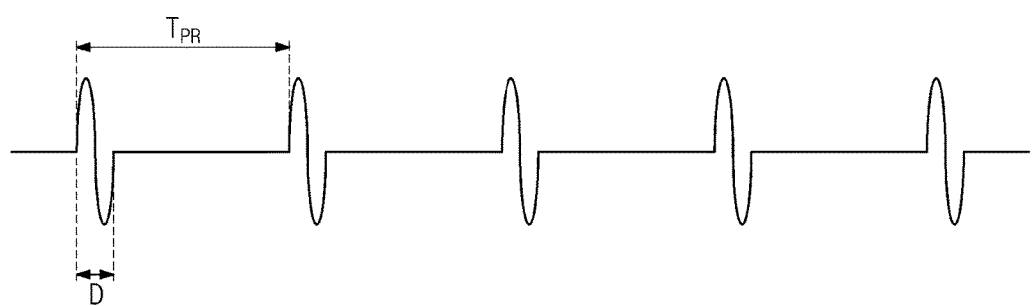
FIG. 3 is a diagram schematically illustrating a waveform of a time-domain pulse signal used to measure a bio signal of a to-be-measured person, according to an exemplary embodiment of the inventive concept.

FIG. 3 is a diagram schematically illustrating a waveform of a time-domain pulse signal used to measure a bio signal of a to-be-measured person, according to an exemplary embodiment of the inventive concept.

Referring to FIG. 3, a pulse signal may be a signal of which the pulse is iterated every pulse iteration period. In exemplary embodiments, the pulse may be an impulse having duration (D) corresponding to a nanosecond unit, and the pulse signal may be a ultra wide band (UWB) in which an impulse is repeated every pulse repetition period $T_{PR}$.

A pulse signal that is transmitted from a transmitter 100 and penetrates a to-be-measured person may be received by an antenna 211, and the received pulse signal may be amplified by an amplifier 212. The amplified pulse signal may be sampled by a sampling unit 213, and the sampled signal may be converted into a digital signal by an analog-to-digital converter 215.

A processing unit 220 may process the digital signal according to a predetermined process to analyze a bandwidth of the received pulse signal and may measure a bio signal of the to-be-measured person, for example, a heartbeat according to a result of analyzing the bandwidth.

Figure 4:
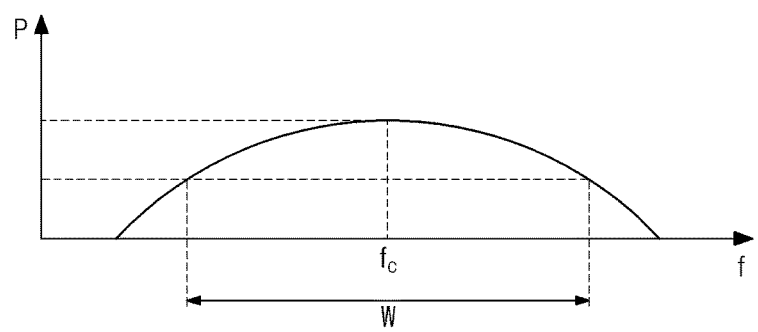
FIG. 4 is a diagram schematically illustrating power spectrum of a pulse signal used to measure a bio signal of a to-be-measured person, according to an exemplary embodiment of the inventive concept.

FIG. 4 is a diagram schematically illustrating power spectrum of a pulse signal used to measure a bio signal of a to-be-measured person, according to an exemplary embodiment of the inventive concept.

As described above, since a pulse signal used to measure a bio signal of a to-be-measured person is a signal in which an impulse having very short duration corresponding to a nanosecond unit is repeated, in a frequency domain, low power spectrum density may be distributed over a very wide bandwidth ranging to several gigahertzes as illustrated in FIG. 4.

According to an exemplary embodiment of the inventive concept, a bio signal such as a heartbeat may be measured by transmitting an ultra-wide band signal to a to-be-measured person and analyzing a bandwidth of a signal penetrating the to-be-measured person. Below, a process that a processing unit performs to measure a heartbeat of a bio signal will be more fully described with reference to accompanying drawings.

Figure 5:
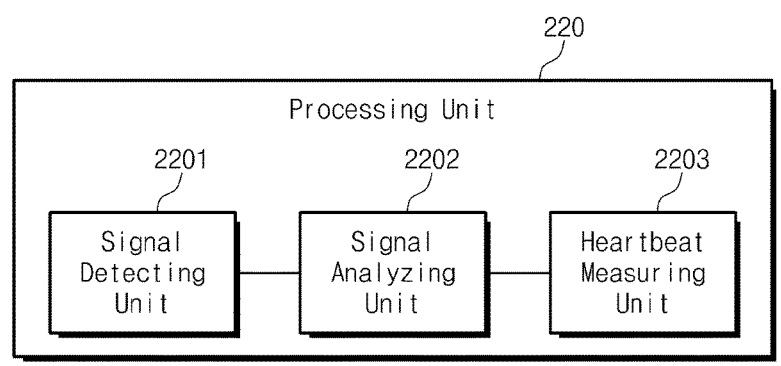
FIG. 5 is a block diagram schematically illustrating a processing unit according to an exemplary embodiment of the inventive concept.

FIG. 5 is a block diagram schematically illustrating a processing unit 220 according to an exemplary embodiment of the inventive concept.

As illustrated in FIG. 5, a processing unit 220 may contain a signal detecting unit 2201, a signal analyzing unit 2202, and a heartbeat measuring unit 2203.

The signal detecting unit 2201 may detect a signal, penetrating a heart of a to-be-measured person, from among a received pulse signal.

Even though a transmitter 100 transmits a pulse signal toward a heart of the to-be-measured person, a portion of the transmitted signal may penetrates an organ different from a heart, for example, a lung and reaches a bio signal measuring apparatus 200.

In this case, the signal detecting unit 2201 may merely detect a signal, penetrating a heart, from among the received pulse signal and may remove a signal penetrating a lung.

In exemplary embodiments, the signal detecting unit 2201 may detect a signal penetrating a heart using the strength of signal.

Since the heart is filled with liquid such as blood and the lung is filled with gas such as air, attenuation of a signal penetrating the heart may be different from that of a signal penetrating the lung.

Since attenuation of a signal penetrating gas is greater than that of a signal penetrating liquid, according to an exemplary embodiment of the inventive concept, the signal detecting unit 2201 may classify a received signal into two groups according to the strength of signal, and may determine a signal belonging to a group of which the strength is small, as a signal penetrating the heart.

In other exemplary embodiments, the signal detecting unit 2201 may detect a signal penetrating the heart using a time when a signal is received.

In detail, the signal detecting unit 2201 may determine a signal, first received, from among signals transmitted at the same time from a transmitter 100, as a signal penetrating a heart.

A signal that the bio signal measuring apparatus 200 first receives may correspond to a signal of which the transmission distance is shortest, and the signal may correspond to a signal that is transmitted in a straight line between a transmitter 100 and the bio signal measuring apparatus 200.

Accordingly, as illustrated in FIG. 1, in the case where the transmitter 100 and the bio signal measuring apparatus 200 are placed on a straight line passing through a heart of a person to be measured, the first received signal may be a signal passing through a heart.

The signal analyzing unit 2203 may analyze a bandwidth of a signal that the signal detecting unit 2201 detects as a signal penetrating a heart. The signal analyzing unit 2203 may measure a heartbeat of the to-be-measured person based on an analysis result of the signal analyzing unit 2202.

Figure 6:
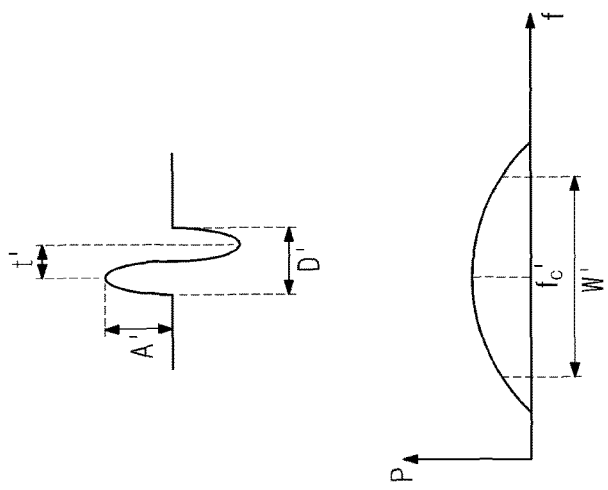
FIGS. 6 and 7 are diagrams schematically illustrating time-domain waveforms and frequency-domain power spectrums after a pulse signal passes through a contracted heart and a dilated heart, according to an exemplary embodiment of the inventive concept.
Figure 6:
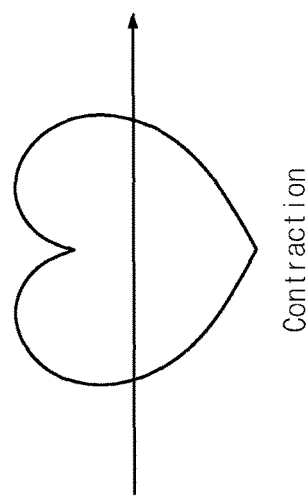
Figure 6:
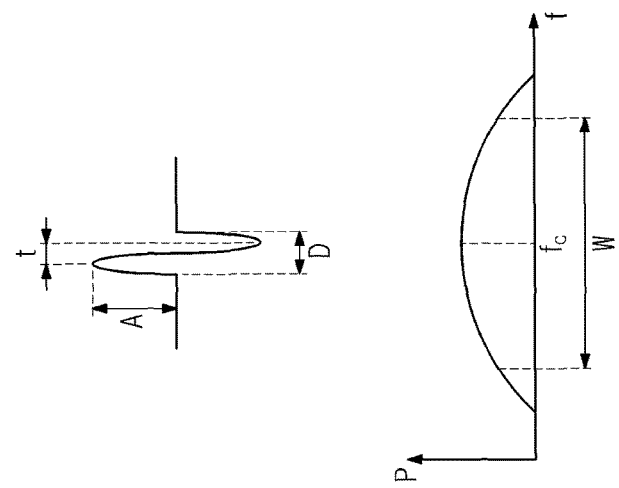
Figure 7:
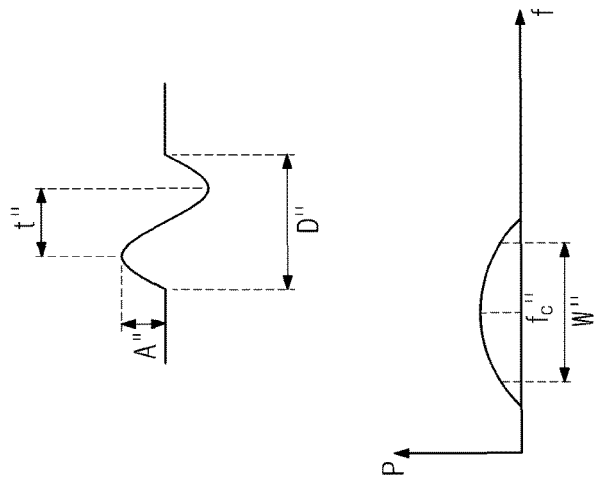
Figure 7:
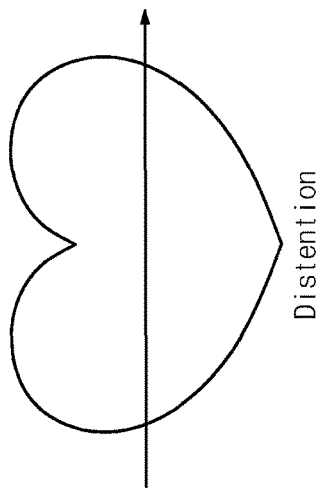
Figure 7:
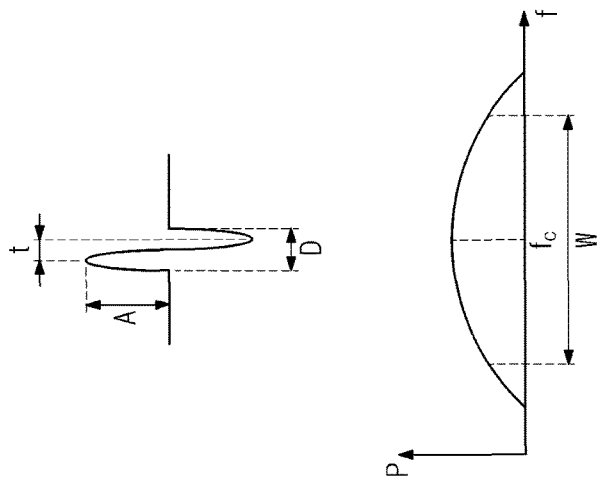

FIGS. 6 and 7 are diagrams schematically illustrating time-domain waveforms and frequency-domain power spectrums after a pulse signal passes through a contracted heart and a dilated heart, according to an exemplary embodiment of the inventive concept.

According to an exemplary embodiment of the inventive concept, in the case where a pulse signal penetrates a heart, a center frequency fc and amplitude A as well as a bandwidth W may decrease, and the decrement may vary according to the size of heart.

For example, as illustrated in FIGS. 6 and 7, it may be assumed that a pulse signal transmitted toward a heart of a to-be-measured person has amplitude A in a time domain and a center frequency fc and a bandwidth W in a frequency domain. Furthermore, it may be assumed that when the size of the heart is reduced due to contraction, the pulse signal transmitted toward the heart has amplitude A' in a time domain and a center frequency fc' and a bandwidth W' in a frequency domain. Furthermore, it may be assumed that when the size of the heart is reduced due to distention, the pulse signal transmitted toward the heart has amplitude A" in a time domain and a center frequency fc" and a bandwidth W" in a frequency domain. According to such assumptions, an amplitude relation between signals may be A>A'>A", a center frequency relation between the signals may be fc>fc'>fc", and a bandwidth relation between the signals may be W>W'>W".

That is, according to an exemplary embodiment of the inventive concept, as the size of heart becomes larger, a center frequency fc of a pulse signal penetrating a heart may become lower, its bandwidth W may become narrower, and its amplitude A may become smaller.

According to an exemplary embodiment of the inventive concept, a processing unit 220 may measure a heartbeat by monitoring a bandwidth W, a center frequency fc, and amplitude A of a received pulse signal to detect contraction and distention of the heart.

In other exemplary embodiments, the processing unit 220 may measure a heartbeat by monitoring variations in a bandwidth W, a center frequency fc, and amplitude A of a received pulse signal to detect contraction and distention of the heart.

Below, an operation in which the processing unit 220 measures a heartbeat using a pulse signal will be more fully described with reference to accompanying drawings.

Figure 8:
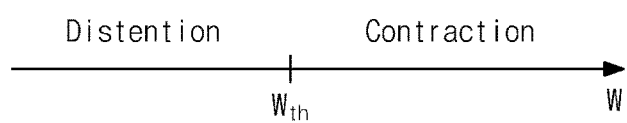
FIG. 8 is a diagram for describing a method for measuring a heartbeat using a bandwidth of a pulse signal, according to an exemplary embodiment of the inventive concept.

FIG. 8 is a diagram for describing a method for measuring a heartbeat using a bandwidth W of a pulse signal, according to an exemplary embodiment of the inventive concept.

According to an exemplary embodiment of the inventive concept, after calculating a bandwidth W of a pulse signal, a processing unit 220 may compare the bandwidth W with a predetermined threshold value to determine whether a heart is contracted or distended.

In detail, referring to FIG. 8, the processing unit 220 may calculate a bandwidth W of the pulse signal. When the bandwidth W is greater than a predetermined bandwidth threshold value $W_{th}$, the processing unit 220 may determine a period of a pulse signal having the bandwidth, as a contraction period of a heart. When the bandwidth W is smaller than the predetermined bandwidth threshold value $W_{th}$, the processing unit 220 may determine a period of a pulse signal having the bandwidth, as a distention period of a heart.

In other words, the processing unit 220 may determine, as a contraction period of a heart, a period where a bandwidth W of a received pulse signal is greater than a predetermined level and may determine, as a distention period of a heart, a period where the bandwidth W of the received pulse signal is smaller than the predetermined level.

Figure 9:
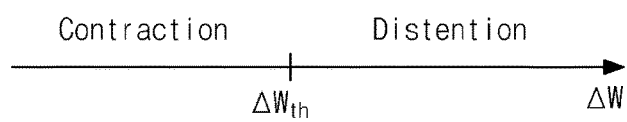
FIG. 9 is a diagram for describing a method for measuring a heartbeat using variations in bandwidth before and after a pulse signal penetrates a heart, according to an exemplary embodiment of the inventive concept.

FIG. 9 is a diagram for describing a method for measuring a heartbeat using variations ΔW in bandwidth before and after a pulse signal penetrates a heart, according to an exemplary embodiment of the inventive concept.

In exemplary embodiments, a processing unit 220 may compare bandwidths W before and after a pulse signal passes through a heart, to calculate a variation ΔW in bandwidth. The processing unit 220 may compare the variation ΔW with a predetermined threshold value to determine whether the heart is contracted or distended.

In detail, the processing unit 220 may compare a bandwidth before the pulse signal penetrates a to-be-measured person and a bandwidth after the pulse signal penetrates the to-be-measured person, to calculate the variation ΔW in bandwidth W before and after the pulse signal penetrates the to-be-measured person. When the variation ΔW in bandwidth is smaller than a predetermined bandwidth variation threshold value $\Delta W_{th}$, a period of the pulse signal having such variation ΔW may be determined as a contraction period of a heart. When the variation ΔW in bandwidth is greater than the bandwidth variation threshold value $\Delta W_{th}$, a period of the pulse signal having such variation ΔW may be determined as a distention period of a heart.

In other words, the processing unit 220 may determine, as a contraction period of a heart, a period where the variation ΔW in bandwidth before and after the pulse signal penetrates the to-be-measured person is smaller than a predetermined level, and may determine, as a distension period, a period where the variation ΔW in bandwidth is greater than the predetermined level.

A heart filled with blood may have a characteristic of a low pass filter. For this reason, as the size of heart becomes larger, a bandwidth of a pulse signal passing through the heart may become narrower. According to an exemplary embodiment of the inventive concept, a heartbeat of a user may be measured using a bandwidth related characteristic.

In addition, according to another exemplary embodiment of the inventive concept, the processing unit 220 may further analyze at least one of a center frequency fc or amplitude A of a pulse signal and may measure a bio signal of a to-be-measured person, based on an analysis result about the bandwidth W and an analysis result about at least one of the center frequency fc or the amplitude A.

Figure 10:
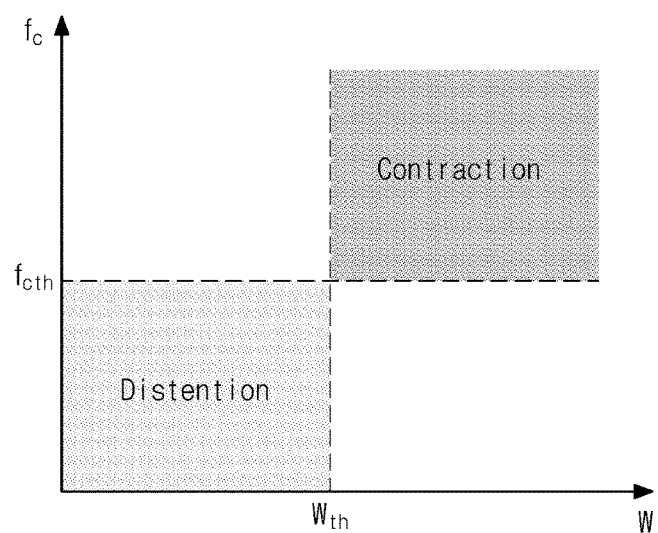
FIG. 10 is a diagram for describing a method for measuring a heartbeat using a bandwidth and a center frequency of a pulse signal, according to an exemplary embodiment of the inventive concept.

FIG. 10 is a diagram for describing a method for measuring a heartbeat using a bandwidth W and a center frequency fc of a pulse signal, according to an exemplary embodiment of the inventive concept.

In exemplary embodiments, a processing unit 220 may further analyze a center frequency fc of a pulse signal as well as a bandwidth W thereof and may determine whether a heart is contracted or distended, based on the analysis result.

In detail, the processing unit 220 may calculate the center frequency fc of a pulse signal. When the center frequency fc is higher than a predetermined center frequency threshold value $f_{cth}$, the processing unit 220 may determine, as a distension period of a heart, a period where a pulse signal has the center frequency fc. When the center frequency fc is lower than the center frequency threshold value $f_{cth}$, the processing unit 220 may determine, as a contraction period of a heart, a period where a pulse signal has the center frequency fc.

In exemplary embodiments, the processing unit 220 may more accurately determine whether a heart is contracted or distended, by measuring a heartbeat using a center frequency fc of a received pulse signal as well as a bandwidth W thereof.

For example, as illustrated in FIG. 10, the processing unit 220 may determine, a contraction period of a heart, a period where a bandwidth W of a pulse signal is greater than a bandwidth threshold value $W_{th}$ and a center frequency fc is higher than a center frequency threshold value $f_{cth}$. In contrast, the processing unit 220 may determine, a distension period of a heart, a period where a bandwidth W of a pulse signal is smaller than the bandwidth threshold value $W_{th}$ and a center frequency fc is lower than the center frequency threshold value $f_{cth}$.

As such, conditions used to determine whether a heart is contracted or distended may increase, thereby reducing an error occurring in measuring a heartbeat and measuring a heartbeat more accurately.

In exemplary embodiments, the processing unit 220 may grade a score based on a difference between a bandwidth W of a received pulse signal and a bandwidth threshold value $W_{th}$ and may grade a score based on a difference between a center frequency fc of the received pulse signal and a center frequency threshold value $f_{cth}$. Next, the processing unit 220 may assign the same or different weights to the score about the bandwidth W and the score about the center frequency fc and may determine whether a heart is contrasted or distended, using a final score obtained by adding the weighted scores. In this case, the reliability of measurement may be enhanced by assigning a greater weight to one, important to measure a heartbeat, from among the bandwidth W and the center frequency fc.

Figure 11:
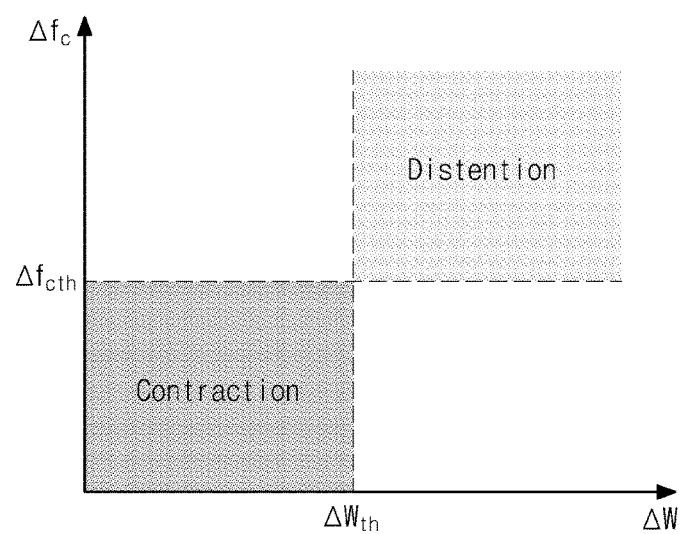
FIG. 11 is a diagram for describing a method for measuring a heartbeat using a bandwidth variation and a center frequency variation of a pulse signal, according to another exemplary embodiment of the inventive concept.

FIG. 11 is a diagram for describing a method for measuring a heartbeat using a bandwidth variation $\Delta W$ and a center frequency variation $\Delta fc$ of a pulse signal, according to another exemplary embodiment of the inventive concept.

In exemplary embodiments, a processing unit 220 may further analyze a center frequency variation $\Delta fc$ of a pulse signal as well as a bandwidth variation $\Delta W$ thereof and may determine whether a heart is contrasted or distended, based on the analysis result.

In detail, the processing unit 220 may compare center frequencies before and after a pulse signal passes through a to-be-measured person, to calculate a center frequency variation $\Delta fc$ before and after the pulse signal passes through the to-be-measured person. When the variation $\Delta fc$ in the center frequency is smaller than a predetermined center frequency variation threshold value $\Delta f_{cth}$, the processing unit 220 may determine, as a contraction period of a heart, a period where the pulse signal has the variation. When the variation $\Delta fc$ in the center frequency is greater than the center frequency variation threshold value $\Delta f_{cth}$, the processing unit 220 may determine, as a distension period of a heart, a period where the pulse signal has the variation.

In exemplary embodiments, the processing unit 220 may more accurately determine whether a heart is contracted or distended, by measuring a heartbeat using a center frequency variation $\Delta fc$ of a received pulse signal as well as a bandwidth variation $\Delta W$ thereof.

For example, as illustrated in FIG. 11, the processing unit 220 may determine, as a contraction period of a heart, a period where a bandwidth variation $\Delta W$ of a pulse signal is smaller than a bandwidth variation threshold value $\Delta W_{th}$ and a center frequency variation $\Delta fc$ is smaller than a center frequency variation threshold value $\Delta f_{cth}$. In contrast, the processing unit 220 may determine, as a distension period of a heart, a period where the bandwidth variation $\Delta W$ of the pulse signal is greater than the bandwidth variation threshold value $\Delta W_{th}$ and the center frequency variation $\Delta fc$ is greater than the center frequency variation threshold value $\Delta f_{cth}$.

In exemplary embodiments, the processing unit 220 may grade a score based on a difference between a bandwidth variation $\Delta W$ of a received pulse signal and a bandwidth variation threshold value $\Delta W_{th}$ and may grade a score based on a difference between a center frequency variation $\Delta fc$ of the received pulse signal and a center frequency variation threshold value $\Delta f_{cth}$. Next, the processing unit 220 may assign the same or different weights to the score about the bandwidth variation $\Delta W$ and the score about the center frequency variation $\Delta fc$ and may determine whether a heart is contrasted or distended, using a final score obtained by adding the weighted scores. In this case, the reliability of measurement may be enhanced by assigning a greater weight to one, important to measure a heartbeat, from among the bandwidth variation $\Delta W$ and the center frequency variation $\Delta fc$.

Figure 12:
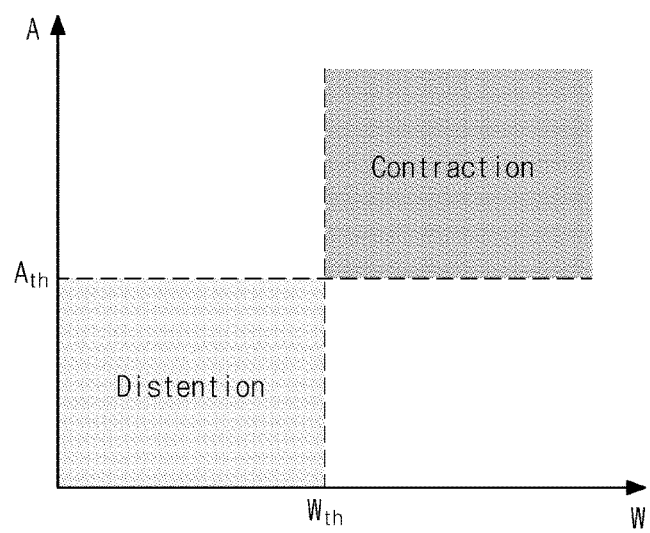
FIG. 12 is a diagram for describing a method for measuring a heartbeat using a bandwidth and amplitude of a pulse signal, according to still another exemplary embodiment of the inventive concept.

FIG. 12 is a diagram for describing a method for measuring a heartbeat using a bandwidth W and amplitude A of a pulse signal, according to still another exemplary embodiment of the inventive concept.

In exemplary embodiments, a processing unit 220 may further analyze amplitude A of a pulse signal as well as a bandwidth W thereof and may determine whether a heart is contrasted or distended, based on the analysis result.

In detail, the processing unit 220 may calculate amplitude A of the pulse signal. When the amplitude A is greater than a predetermined amplitude threshold value $A_{th}$, the processing unit 220 may determine, as a contraction period of a heart, a period where the pulse signal has the amplitude. When the amplitude A is smaller than the amplitude threshold value $A_{th}$, the processing unit 220 may determine, as a distension period of a heart, a period where the pulse signal has the amplitude.

In exemplary embodiments, the processing unit 220 may more accurately determine whether a heart is contracted or distended, by measuring a heartbeat using amplitude A of a received pulse signal as well as a bandwidth W thereof.

For example, as illustrated in FIG. 12, the processing unit 220 may determine, as a contraction period of a heart, a period where a bandwidth W of a pulse signal is greater than a bandwidth threshold value $W_{th}$ and amplitude A is greater than an amplitude threshold value $A_{th}$. In contrast, the processing unit 220 may determine, as a distension period of a heart, a period where the bandwidth W of the pulse signal is smaller than the bandwidth threshold value $W_{th}$ and the amplitude A is smaller than the amplitude threshold value $A_{th}$.

In exemplary embodiments, the processing unit 220 may grade a score based on a difference between a bandwidth W of a received pulse signal and a bandwidth threshold value $W_{th}$ and may grade a score based on a difference between amplitude A of the received pulse signal and an amplitude threshold value $A_{th}$. Next, the processing unit 220 may assign the same or different weights to the score about the bandwidth W and the score about the amplitude A and may determine whether a heart is contrasted or distended, using a final score obtained by adding the weighted scores. In this case, the reliability of measurement may be enhanced by assigning a greater weight to one, important to measure a heartbeat, from among the bandwidth W and the amplitude A.

Figure 13:
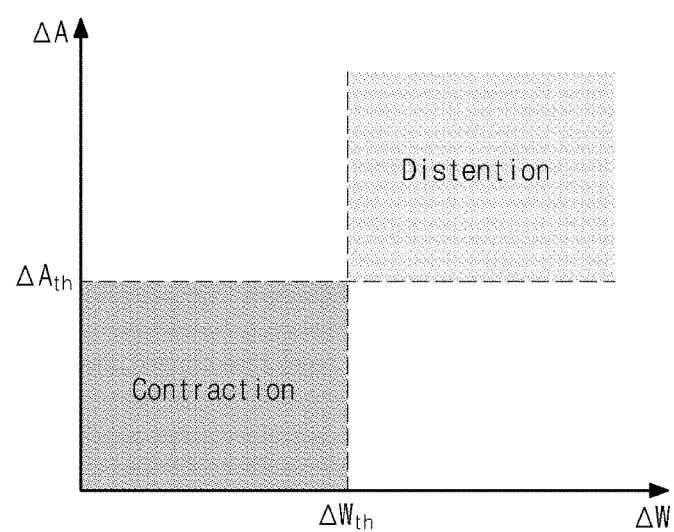
FIG. 13 is a diagram for describing a method for measuring a heartbeat using a bandwidth variation and an amplitude variation of a pulse signal, according to still another exemplary embodiment of the inventive concept.

FIG. 13 is a diagram for describing a method for measuring a heartbeat using a bandwidth variation $\Delta W$ and an amplitude variation $\Delta A$ of a pulse signal, according to still another exemplary embodiment of the inventive concept.

In exemplary embodiments, a processing unit 220 may further analyze an amplitude variation $\Delta A$ of a pulse signal as well as a bandwidth variation $\Delta W$ thereof and may determine whether a heart is contrasted or distended, based on the analysis result.

In detail, the processing unit 220 may compare amplitudes of a pulse signal before and after the pulse signal passes through a heart of a to-be-measured person, to calculate an amplitude variation $\Delta A$. When the amplitude variation $\Delta A$ is smaller than a predetermined amplitude variation threshold value $\Delta A_{th}$, the processing unit 220 may determine, as a contraction period of a heart, a period where the pulse signal has the amplitude variation $\Delta A$. When the amplitude variation $\Delta A$ is greater than the amplitude variation threshold value $\Delta A_{th}$, the processing unit 220 may determine, as a distension period of a heart, a period where the pulse signal has the amplitude variation $\Delta A$.

In exemplary embodiments, the processing unit 220 may more accurately determine whether a heart is contracted or distended, by measuring a heartbeat using an amplitude variation $\Delta A$ of a received pulse signal as well as a bandwidth variation $\Delta W$ thereof.

For example, as illustrated in FIG. 13, the processing unit 220 may determine, as a contraction period of a heart, a period where a bandwidth variation $\Delta W$ of a pulse signal is smaller than a bandwidth variation threshold value $\Delta W_{th}$ and an amplitude variation $\Delta A$ is smaller than an amplitude variation threshold value $\Delta A_{th}$. In contrast, the processing unit 220 may determine, as a distension period of a heart, a period where the bandwidth variation $\Delta W$ of the pulse signal is greater than the bandwidth variation threshold value $\Delta W_{th}$ and the amplitude variation $\Delta A$ is greater than the amplitude variation threshold value $\Delta A_{th}$.

In exemplary embodiments, the processing unit 220 may grade a score based on a difference between a bandwidth variation $\Delta W$ of a received pulse signal and a bandwidth variation threshold value $\Delta W_{th}$, and may grade a score based on a difference between an amplitude variation $\Delta A$ of the received pulse signal and an amplitude variation threshold value $\Delta A_{th}$. Next, the processing unit 220 may assign the same or different weights to the score about the bandwidth variation $\Delta W$ and the score about the amplitude variation $\Delta A$ and may determine whether a heart is contrasted or distended, using a final score obtained by adding the weighted scores. In this case, the reliability of measurement may be enhanced by assigning a greater weight to one, important to measure a heartbeat, from among the bandwidth variation $\Delta W$ and the amplitude variation $\Delta A$.

Embodiments of the inventive concept may be illustrated as a heartbeat is measured using a result of analyzing a center frequency fc or amplitude A of a pulse signal as well as a result of analyzing a bandwidth W thereof or a result of analyzing a center frequency variation $\Delta$fc or an amplitude variation $\Delta A$ as well as a result of analyzing a bandwidth variation $\Delta W$. However, the scope and spirit of the inventive concept may not be limited thereto. For example, a heartbeat may be measured using a bandwidth W, a center frequency fc, and amplitude A, using a bandwidth variation $\Delta W$, a center frequency variation $\Delta$fc, and an amplitude variation $\Delta A$, or using a combination of two or more of the bandwidth W, the center frequency fc, the amplitude A, the bandwidth variation $\Delta W$, the center frequency variation $\Delta$fc, and the amplitude variation $\Delta A$.

According to an exemplary embodiment of the inventive concept, the processing unit 220 may convert a received pulse signal from a time domain to a frequency domain and may measure a center frequency or a bandwidth of a pulse signal in the time domain. At this time, the processing unit 220 may obtain a frequency spectrum of pulse signal using a Fourier transform algorithm. However, the scope and spirit of the inventive concept may not be limited thereto.

According to another exemplary embodiment of the inventive concept, the processing unit may process a received pulse signal in a time domain without converting into a frequency domain to analyze a bandwidth or a center frequency.

In exemplary embodiments, the processing unit 220 may measure duration D of a pulse included in a pulse signal in a time domain and may analyze a bandwidth W of a pulse signal using the duration D.

Figure 14:
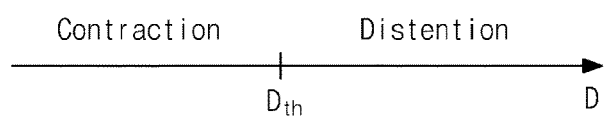
FIG. 14 is a diagram for describing a method for measuring a heartbeat by analyzing a bandwidth using duration of a pulse signal, according to still another exemplary embodiment of the inventive concept.

FIG. 14 is a diagram for describing a method for measuring a heartbeat by analyzing a bandwidth W using duration D of a pulse signal, according to still another exemplary embodiment of the inventive concept.

For example, referring to FIG. 14, a processing unit 220 may compare duration D with a duration threshold value $D_{th}$ corresponding to the above-described bandwidth threshold value $W_{th}$. When the duration D is shorter than the bandwidth threshold value $W_{th}$, a period where a pulse signal has the duration may be determined as a contraction period of a heart. When the duration D is longer than the bandwidth threshold value $W_{th}$, a period where a pulse signal has the duration may be determined as a distension period of a heart.

Furthermore, the processing unit 220 may measure duration D of a pulse included in a pulse signal in a time domain and may compare durations before and after the pulse signal passes through a to-be-measured person, to calculate a duration variation $\Delta D$ before and after the pulse signal passes through a to-be-measured person. Next, the processing unit 220 may analyze a bandwidth variation $\Delta W$ using the duration variation $\Delta D$.

For example, the processing unit 220 may compare the duration variation $\Delta D$ with a duration variation threshold value $\Delta D$th corresponding to the bandwidth variation threshold value $\Delta W_{th}$. When the duration variation $\Delta D$ is smaller than the duration variation threshold value $\Delta D$th, the processing unit 220 may determine, as a contraction period of a heart, a period where a pulse signal has the duration variation $\Delta D$. When the duration variation $\Delta D$ is greater than the duration variation threshold value $\Delta D$th, the processing unit 220 may determine, as a distension period of a heart, a period where a pulse signal has the duration variation $\Delta D$.

Furthermore, the processing unit 220 may analyze not only a bandwidth W based on duration D of a pulse signal, but it may analyze a center frequency fc based on a time difference t (in FIGS. 6 and 7) between a pulse portion having positive amplitude and pulse portion having negative amplitude.

Figure 15:
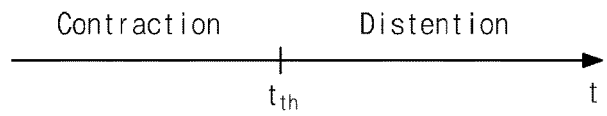
FIG. 15 is a diagram for describing a method for measuring a heartbeat by analyzing a center frequency using a time difference t between a pulse portion having positive amplitude and a pulse portion having negative amplitude, according to a further exemplary embodiment of the inventive concept.

FIG. 15 is a diagram for describing a method for measuring a heartbeat by analyzing a center frequency fc using a time difference t between a pulse portion having positive amplitude and a pulse portion having negative amplitude, according to a further exemplary embodiment of the inventive concept.

For example, referring to FIG. 15, a processing unit 220 may measure a time difference t of a pulse signal in a time domain and may compare the measured time difference t with a time difference threshold value $t_{th}$ corresponding to the above-described center frequency threshold value $f_{cth}$. When the time difference t is smaller than the time difference threshold value $t_{th}$, the processing unit 220 may determine, as a contraction period of a heart, a period where the pulse signal has the time difference t. When the time difference t is greater than the time difference threshold value $t_{th}$, the processing unit 220 may determine, as a distension period of a heart, a period where the pulse signal has the time difference t.

Also, the processing unit 220 may measure the time difference t in the time domain and may calculate a time difference variation $\Delta t$ by comparing time differences before and after the pulse signal penetrates a person to be measured. The processing unit 220 may analyze a variation $\Delta$fc in a center frequency fc using the variation $\Delta t$ in the time difference.

For example, the processing unit 220 may compare the time difference variation $\Delta t$ with a time difference variation threshold value $\Delta t_{th}$ corresponding to the above-described center frequency variation threshold value $\Delta f_{cth}$. When the time difference variation $\Delta t$ is smaller than the time difference variation threshold value $\Delta t_{th}$, the processing unit 220 may determine, as a contraction period of a heart, a period where the pulse signal has the time difference variation $\Delta t$. When the time difference variation $\Delta t$ is greater than the time difference variation threshold value $\Delta t_{th}$, the processing unit 220 may determine, as a distension period of a heart, a period where the pulse signal has the time difference variation $\Delta t$.

As such, a heartbeat may be measured by directly measuring duration D or a time difference t in a time domain, not converting a received pulse signal into a frequency-domain signal to measure a bandwidth W or a center frequency fc, thereby processing a signal more simply and making it easy to implement a system.

A bio signal measuring apparatus and a user monitoring system according to an exemplary embodiment of the inventive concept may perform measurement of a bio signal of a user including a heartbeat and monitoring of a user condition, using a bandwidth of a pulse signal penetrating a body of the user. Accordingly, a bio signal may be accurately measured without influence of movement of the user.

Furthermore, according to an embodiment of the inventive concept, power consumption may be reduced by measuring a bio signal with low-performance hardware for processing a signal in a low speed in measuring a bio signal of a to-be-measured person using a high-speed pulse signal.

To this end, returning to FIG. 2, the sampling unit 213 may sample a portion of a pulse included in the pulse signal such that portions respectively sampled from a plurality of pulses are different.

Figure 16:
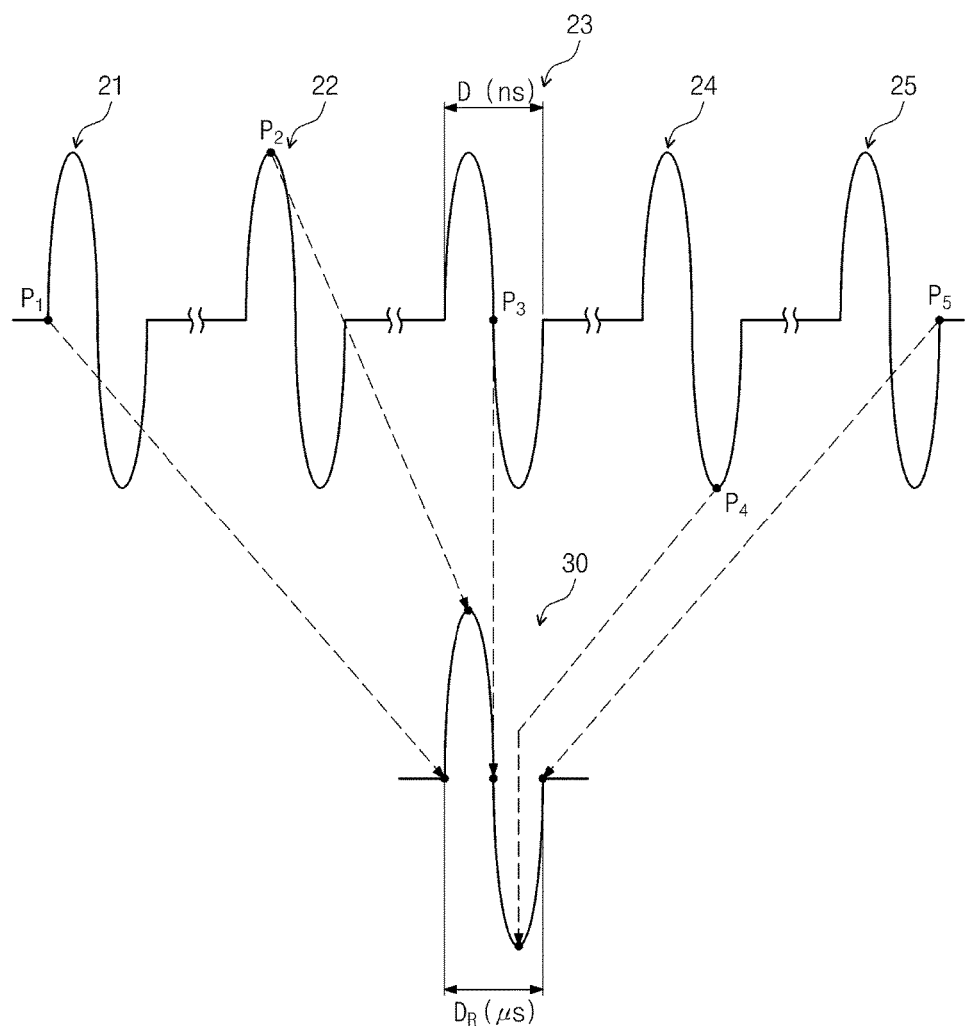
FIGS. 16 and 17 are diagrams for describing a method for a sampling unit sampling a pulse signal, according to an exemplary embodiment of the inventive concept.
Figure 17:
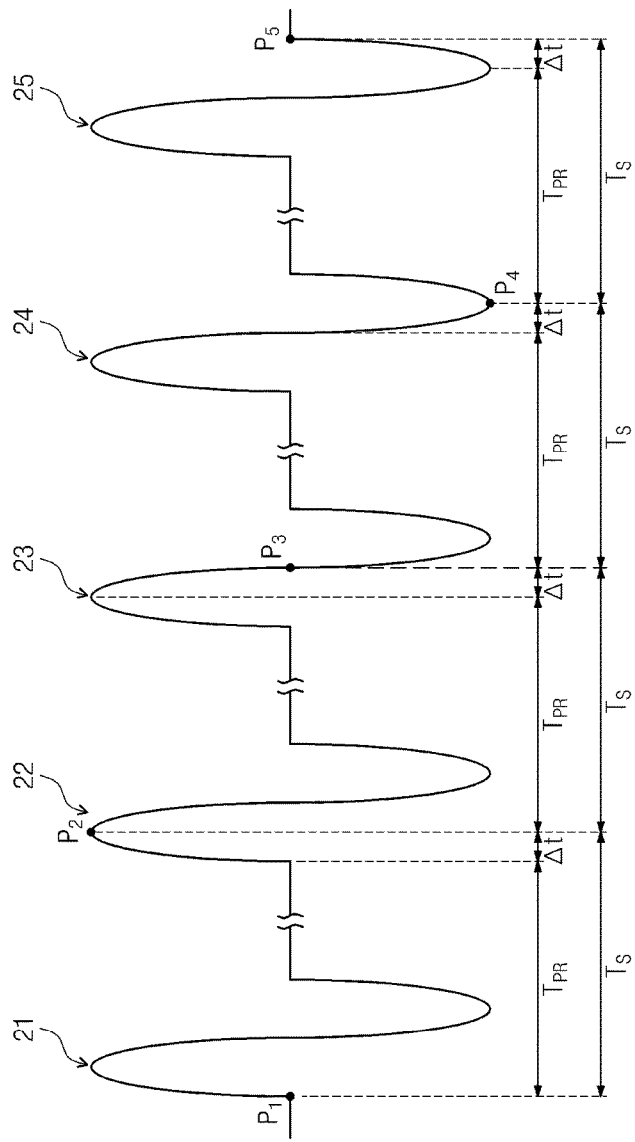

FIGS. 16 and 17 are diagrams for describing a method for a sampling unit 213 sampling a pulse signal, according to an exemplary embodiment of the inventive concept.

A sampling unit 213 may sample a pulse included in a pulse signal partially, not overall.

For example, referring to FIG. 16, the sampling unit 213 may sample portions P1 to P5 of five pulses 21 to 25 included in a pulse signal. At this time, points where the pulses 21 to 25 are respectively sampled may be different from each other.

In detail, a point where a first pulse 21 of the pulse signal is sampled may be a start point P1 of the pulse. A second pulse 22 of the pulse signal is sampled may be a point P2 corresponding to a quarter of duration D of the pulse. A third pulse 23 of the pulse signal is sampled may be a point P3 corresponding to half the duration D of the pulse. A fourth pulse 24 of the pulse signal is sampled may be a point P4 corresponding to three-quarters of duration D of the pulse. A fifth pulse 25 of the pulse signal is sampled may be an end point P5 of the pulse.

As such, the sampling unit 213 may sample a portion of each pulse, not the entirety of each pulse included in a pulse signal. In particular, the sampling unit 213 may sample different portions of the pulses.

Accordingly, a reconstruction pulse 30 reconstructed by sampling may have longer duration $D_R$ in comparison with pulses 21 to 25 before sampling so as to be converted into a low-speed signal.

For example, as illustrated in FIG. 16, if pulses 21 to 25 used to measure a bio signal of a to-be-measured person is a high-speed impulse having duration D corresponding to a nanosecond unit, the reconstruction pulse 30 reconstructed by sampling may be converted into a low-speed signal having duration $D_R$ corresponding to a microsecond unit.

According to an exemplary embodiment of the inventive concept, sampling of the pulses may be performed every predetermined time, which is obtained by adding a predetermined sampling interval to a pulse repetition period of a pulse signal.

For example, referring to FIG. 17, sampling of each pulse may be performed every $T_S$, a time obtained by adding a sampling interval $\Delta t$ to a pulse repetition period $T_{PR}$ of a pulse signal.

Accordingly, the sampling unit 213 may sample different portions P1 to P5 of pulses 21 to 25, that is, may perform sampling at different times of duration D.

In exemplary embodiments, the sampling interval $\Delta t$ may be predetermined and may then be set to a bio signal measuring apparatus 200. Furthermore, the pulse repetition period $T_{PR}$ may be predetermined and may be then set to a transmitter 100 and the bio signal measuring apparatus 200.

In exemplary embodiments, the bio signal measuring apparatus 200 may be provided with information about the pulse repetition period $T_{PR}$ from the transmitter 100.

In FIGS. 16 and 17, one reconstruction pulse 30 may be obtained by sampling five pulses 21 to 25 under a condition where the sampling interval $\Delta t$ is set to a quarter of duration D. However, the scope and spirit of the inventive concept may not be limited thereto. For example, duration $D_R$ of a reconstruction pulse may be adjusted by increasing or decreasing the sampling interval $\Delta t$.

For example, in the case where the sampling interval $\Delta t$ is set to three-quarters of the duration D, the duration $D_R$ of the reconstruction pulse may become shorter than that of the reconstruction pulse 30 illustrated in FIG. 16. In the case where the sampling interval $\Delta t$ is set to one-eighth of the duration D, the duration $D_R$ of the reconstruction pulse may become longer than that of the reconstruction pulse 30 illustrated in FIG. 16.

Furthermore, in FIGS. 16 and 17, the sampling unit 213 may be illustrated as sampling a pulse at a time of duration of the pulse. However, the number of sampling per pulse may be changed to two or more, not limited to one.

Figure 18:
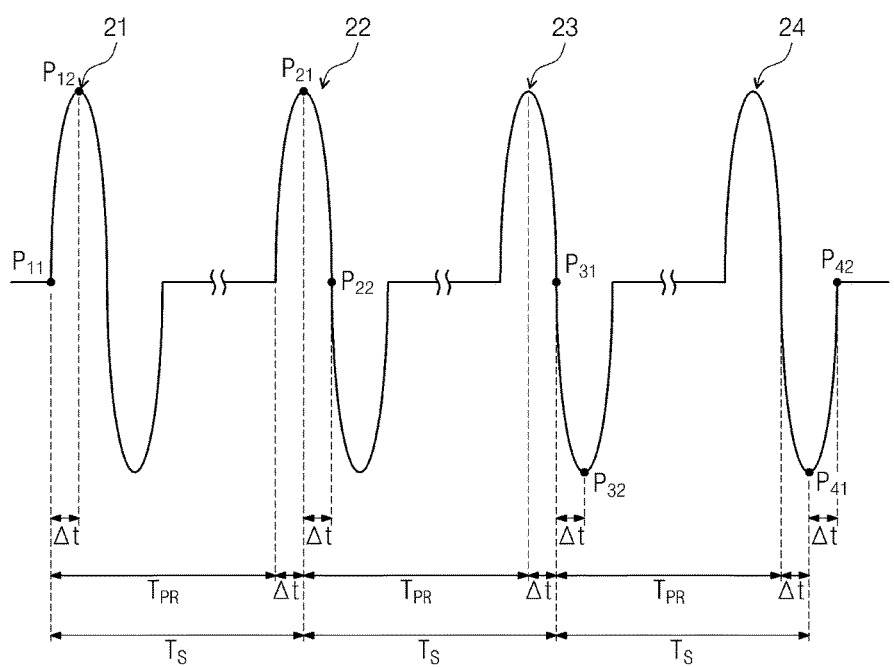
FIG. 18 is a diagram for describing a method in which a sampling unit samples a pulse signal, according to another exemplary embodiment of the inventive concept.

FIG. 18 is a diagram for describing a method in which a sampling unit 213 samples a pulse signal, according to another exemplary embodiment of the inventive concept.

According to another exemplary embodiment of the inventive concept, a sampling unit 213 may sample a pulse at a plurality of times of pulse duration D.

For example, as illustrated in FIG. 18, the sampling unit 213 may sample a pulse two times, and each pulse may be sampled every $T_S$, a time obtained by adding a sampling interval $\Delta t$ to a pulse repetition period $T_{PR}$.

Accordingly, a first pulse 21 of a pulse signal may be sampled at a start point P11 of a pulse and a point P12 corresponding to a quarter of duration D. A second pulse 22 may be sampled at a point P21 corresponding to a quarter of the duration D and a point P22 corresponding to half the duration D. A third pulse 23 may be sampled at a point P31 corresponding to half the duration D and a point P32 corresponding to third-quarters of the duration D. A fourth pulse 24 may be sampled at a point P41 corresponding to third-quarters of the duration D and an end point P42 of the pulse.

In exemplary embodiments, intervals between sampling points in the pulse duration D may be the same as the sampling interval $\Delta t$.

For example, referring to FIG. 18, an interval between sampling points P11 and P12 in the duration D of the first pulse 21 may correspond to a quarter of the duration D, that is, may be the same as the sampling interval $\Delta t$. Likewise, an interval between sampling points in the duration D of each of the second to fourth pulses 22 to 24 may correspond to a quarter of the duration D, that is, may be the same as the sampling interval $\Delta t$.

As such, in the case where the sampling unit 213 samples a pulse at a plurality of times of pulse duration D, a processing unit 220 may determine an average of sampling values, sampled at different points in the pulse duration D, from among sampling values obtained by sampling a plurality of pulses, as a sampling value of a corresponding point.

For example, referring to FIG. 18, the processing unit 220 may average sampling values, sampled at different points in the pulse duration D, for example, P12 and P21 corresponding to a quarter of the pulse duration D, from among eight sampling values obtained by sampling the first to fourth pulses 21 to 24 and may determine the average value as a sampling value of the point.

Likewise, the processing unit 220 may average sampling values sampled at different points P22 and P31 corresponding to half the pulse duration D and may determine the average value as a sampling value of the point. Sampling values of other points may be determined according to the above-described method.

According to the above-described embodiment, a signal to noise ratio (SNR) of a reconstruction pulse obtained from sampling may increase, thus improving measurement reliability about a bio signal.

In FIG. 18, an embodiment of the inventive concept is exemplified as the sampling unit 213 samples a pulse at two times of the pulse duration D. However, the scope and spirit of the inventive concept may not be limited thereto. For example, the number of sampling per pulse may be set to three or more, not limited to two. In this case, a signal to noise ratio (SNR) of a reconstruction pulse may be further improved.

The inventive concept, the sampling unit 213 may be implemented with a mixer including a switch that is closed every sampling period $T_S(=T_{PR}+\Delta t)$ or with a sampler further including a capacitor. However, the scope and spirit of the inventive concept may not be limited thereto.

Furthermore, as will be described later, measurement accuracy may be improved by excluding interference due to reflected signals transmitted through a multi-path and using a pulse signal transmitted through a direct path between a transmitter and a receiver, in measuring a bio signal.

Figure 19:
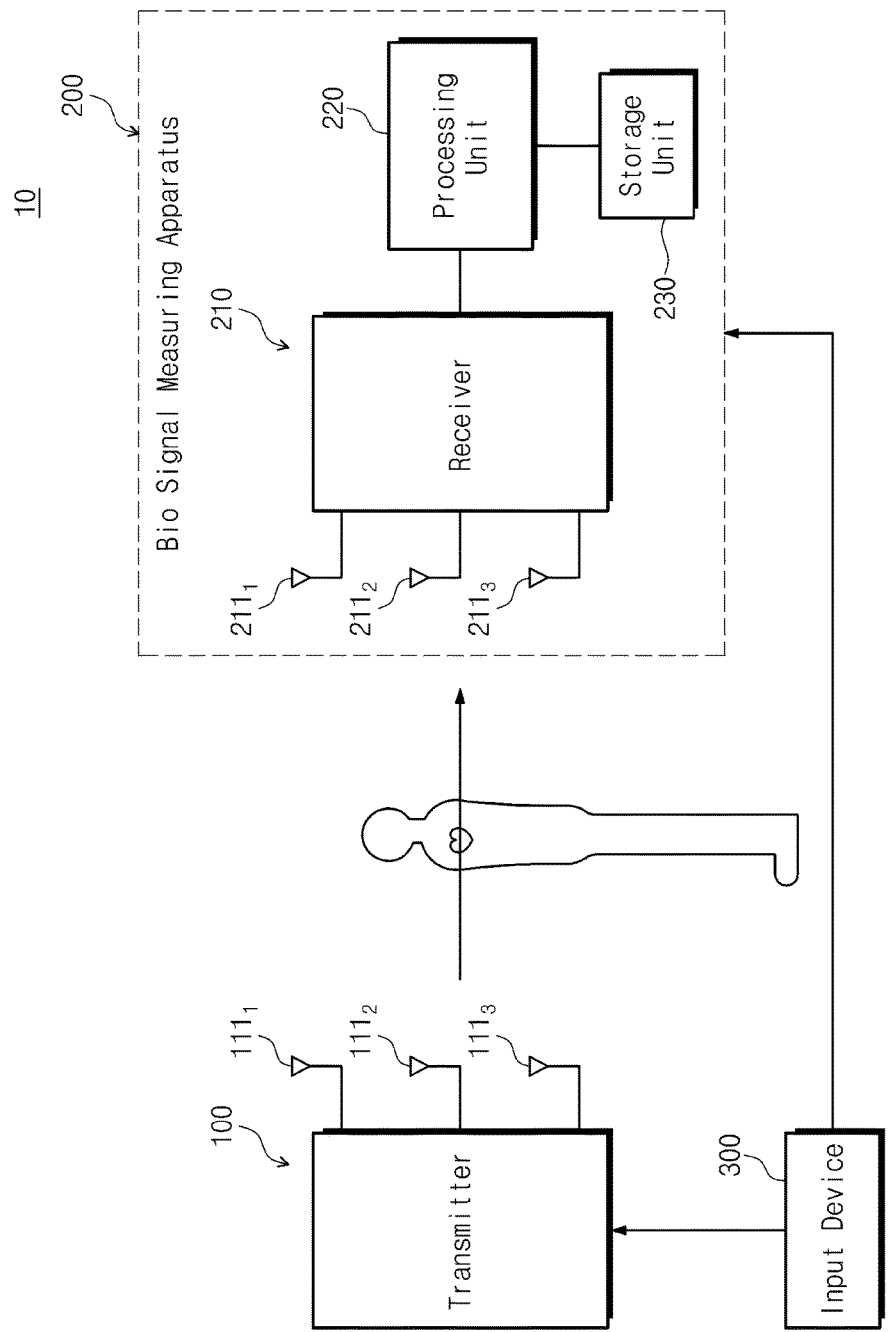
FIG. 19 is a block diagram schematically illustrating a user monitoring system according to another exemplary embodiment of the inventive concept.

FIG. 19 is a block diagram schematically illustrating a user monitoring system 10 according to another exemplary embodiment of the inventive concept.

As illustrated in FIG. 19, a user monitoring system 10 may contain a transmitter 100 and a bio signal measuring apparatus 200. The transmitter 100 may contain at least one antenna 1111, 1112, and 1113, and a receiver 210 of the bio signal measuring apparatus 200 may include at least one antenna 2111, 2112, and 2113.

Below, the inventive concept will be described as each of the transmitter 100 and the receiver 210 has a plurality of antennas. In some embodiments, however, one of the transmitter 100 and the receiver 210 may include one antenna. Furthermore, each of the transmitter 100 and the receiver 210 may have an antenna.

The transmitter 100 may transmit pulse signals through a plurality of antennas 1111, 1112, and 1113 at different times. The receiver 210 may receive and reconstruct a pulse signal penetrating a to-be-measured person through a plurality of antennas 2111, 2112, and 2113.

Furthermore, the bio signal measuring apparatus 200 may include a processing unit 220, and the processing unit 220 may process the reconstructed pulse signal to analyze at least one of a bandwidth, a center frequency, or amplitude of the pulse signal and may measure a bio signal of the to-be-measured person based on the analysis result.

A method in which the processing unit 220 measures a bio signal of a to-be-measured person, for example, a heartbeat using the bandwidth, the center frequency, or the amplitude of the pulse signal may be the same as that described with reference to FIGS. 5 to 15.

Below, the transmitter 100 and the receiver 210 illustrated in FIG. 19 will be described first of all. In the case where the user monitoring system 10 is installed at a vehicle to monitor passengers, arrangements and applications about an antenna array included in the transmitter 100 and an antenna array included in the receiver 210 will be described.

Figure 20:
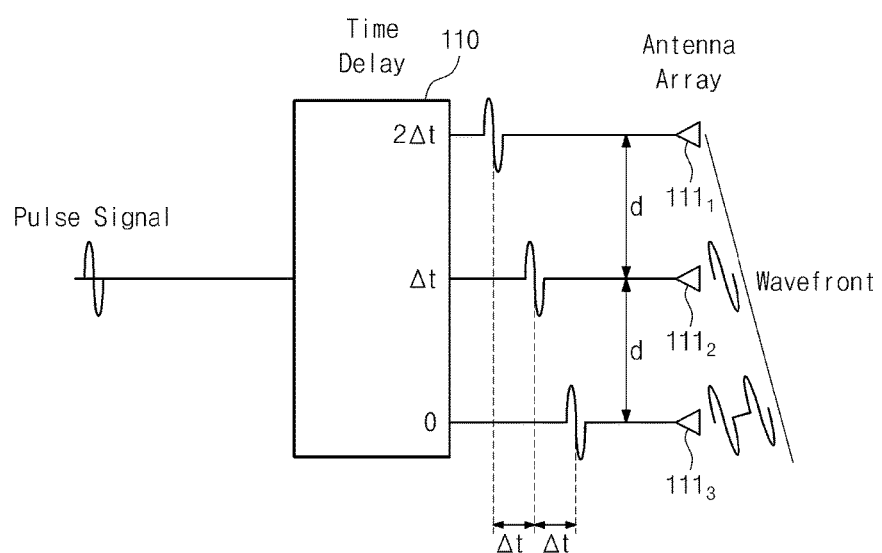
FIG. 20 is a diagram for describing a method in which a transmitter transmits pulse signals, according to another exemplary embodiment of the inventive concept.

FIG. 20 is a diagram for describing a method in which a transmitter 100 transmits pulse signals, according to another exemplary embodiment of the inventive concept.

As illustrated in FIG. 20, a transmitter 100 may transmit pulse signals through a plurality of antennas 1111, 1112, and 1113 at different times.

The transmitter 100 may contain a delay unit 110 to transmit pulse signals through the antennas 1111, 1112, and 1113 at different times.

In exemplary embodiments, the delay unit 110 may provide the v with pulse signals obtained by delaying a pulse signal by different delay times.

For example, referring to FIG. 20, the delay unit 110 may apply different time delays, for example, $2\Delta t$, $\Delta t$, and 0 to a pulse signal provided through RF feed and may provide the delayed pulse signals to the antennas 1111, 1112, and 1113, respectively.

In this case, a signal propagation direction, that is, a wavefront may be determined according to a distance d between antennas and a time difference $\Delta t$ between pulse signals transmitted through antennas.

According to an exemplary embodiment of the inventive concept, a wavefront of a pulse signal transmitted from the transmitter 100 may be set to face the receiver 210. That is, a user monitoring system 10 may previously determine positions of the transmitter 100 and the receiver 210, a distance d between antennas, and a time difference $\Delta t$ between pulse signals to allow a measuring part of a to-be-measured person, for example, a heart to be located on a straight line between the transmitter 100 and the receiver 210.

Figure 21:
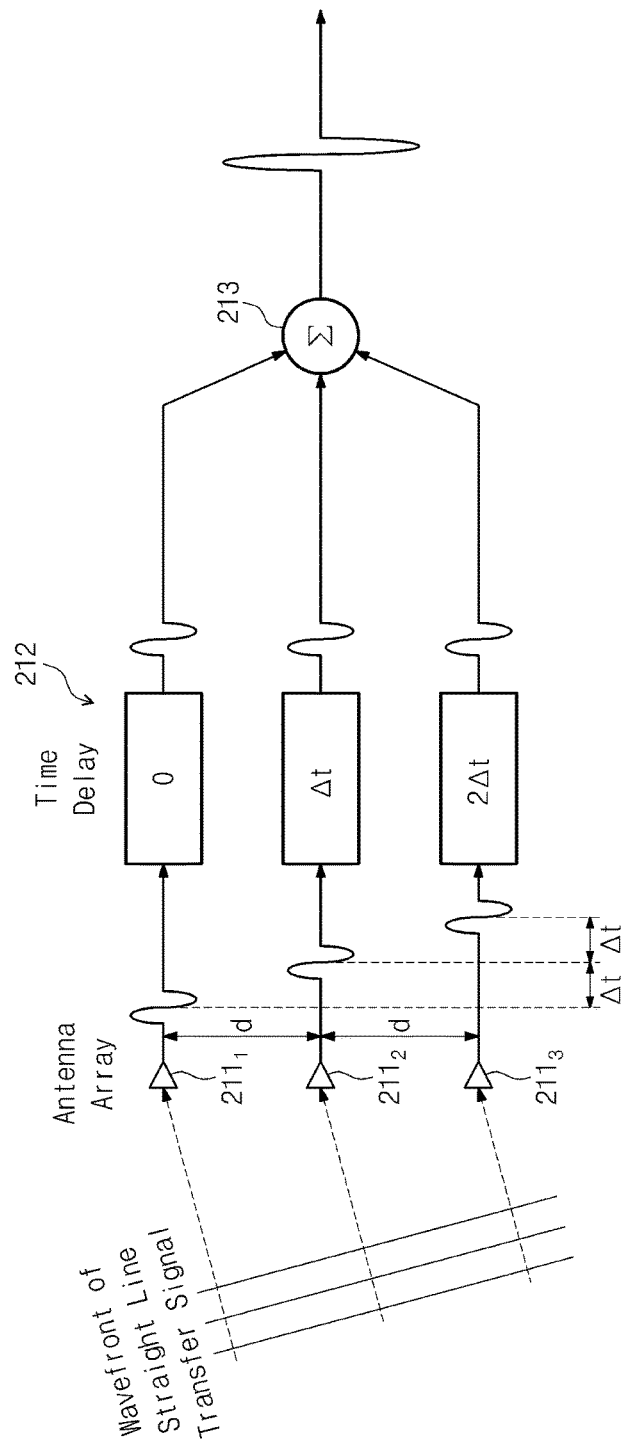
FIG. 21 is a diagram for describing a method in which a receiver receives a pulse signal, according to another exemplary embodiment of the inventive concept.

FIG. 21 is a diagram for describing a method in which a receiver 210 receives a pulse signal, according to another exemplary embodiment of the inventive concept.

As illustrated in FIG. 21, pulse signals transmitted through straight line paths may be received through a plurality of antennas 2111, 2112, and 2113. According to an exemplary embodiment of the inventive concept, a receiver 210 may contain a delay unit 212 and an adder 213, to obtain a pulse signal, to be used to measure a bio signal, from among the pulse signals received.

The delay unit 212 may apply different delays to the pulse signals which the antennas 2111, 2112, and 2113 of the receiver 210 receive. The adder 213 may add a plurality of pulse signals that the delay unit 212 outputs.

Referring to FIG. 21, a pulse signal received through each antenna may be delayed by a delay applied to a corresponding pulse signal of a transmitter 100, and the delay unit 212 may apply delays used at the transmitter 100, that is, 0, $\Delta t$, and $2\Delta t$ to the pulse signals, respectively. Phases of pulse signals transmitted through straight line paths between the transmitter 100 and the receiver 210 may be adjusted so as to have the same values.

Afterwards, the adder 213 may reconstruct a pulse signal by adding phase-adjusted pulse signals from the delay unit 212. In exemplary embodiments, constructive interference may occur due to phase adjustment and adding about pulse signals transmitted through straight line paths in the receiver 210.

Figure 22:
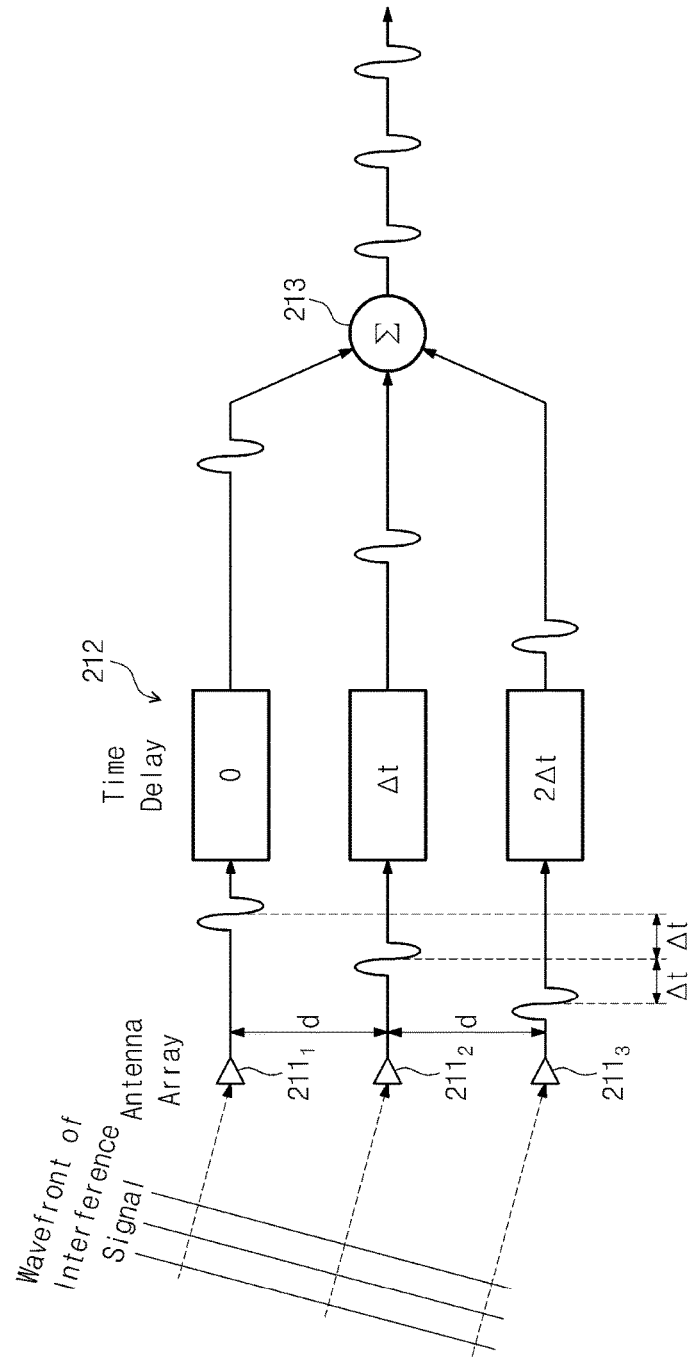
FIG. 22 is a diagram for describing an interference signal receiving method of a receiver, according to another exemplary embodiment of the inventive concept.

FIG. 22 is a diagram for describing an interference signal receiving method of a receiver 210, according to another exemplary embodiment of the inventive concept.

Unlike a signal transmitted through a straight line, a signal reflected and received through a multi-path may lower measurement accuracy about a bio signal. According to an exemplary embodiment of the inventive concept, a receiver 210 may exclude an interference signal transmitted through a multi-path, not a predetermined straight line path, in measuring a bio signal.

Referring to FIG. 22, interference signals received through antennas may be delayed by delays, applied at a transmission stage, that is, 0, Δt, and 2Δt, by a delay unit 212. Unlike signals transmitted through straight line paths illustrated in FIG. 21, phase differences between pulse signals corresponding to interference signals may become greater by the delay unit 212.

Accordingly, a pulse signal added by an adder 213 may be formed of a plurality of pulses having small amplitude without constructive interference as illustrated in FIG. 21.

According to an exemplary embodiment of the inventive concept, a processing unit 220 may select a pulse signal, having amplitude greater than a predetermined threshold value, from among pulse signals from the receiver 210 and may measure a bio signal of a to-be-measured person based on the selected pulse signal. In this case, the processing unit 220 may scale down a pulse signal of which the amplitude is amplified due to the constructive interference, so as to have an amplitude level of a pulse signal before constructive interference.

According to an exemplary embodiment of the inventive concept, the transmitter 100 and the receiver 210 may be synchronized to share a clock signal. For example, the transmitter 100 may transmit information about a clock signal used in the transmitter 100 to the receiver 210 to allow the transmitter 100 and the receiver 210 to share a clock signal. This may mean that the transmitter 100 and the receiver 210 are synchronized. The information about the clock signal may be transferred through a cable, but in some embodiments, it may be wirelessly transmitted.

According to an exemplary embodiment of the inventive concept, a vehicle may be equipped with the user monitoring system 10 to monitor passengers of the vehicle.

Figure 23:
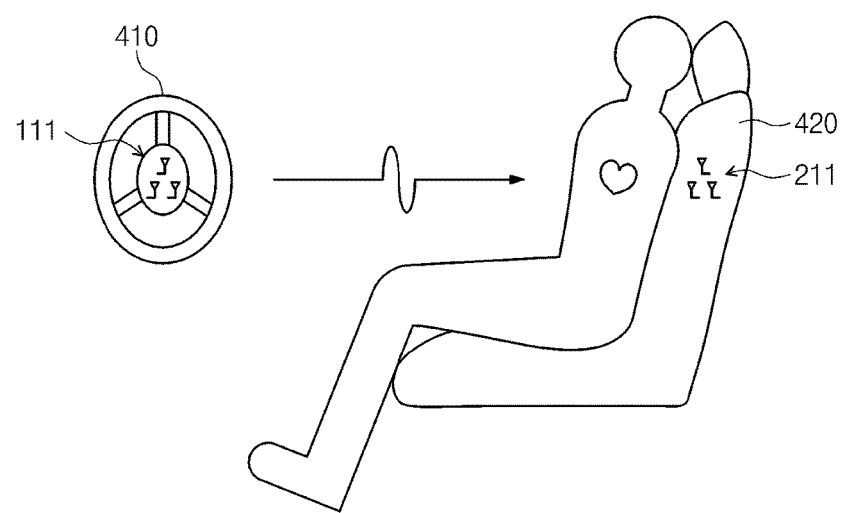
FIG. 23 is a diagram schematically illustrating arrangements of transmitter antennas and receiver antennas in a vehicle according to an exemplary embodiment of the inventive concept.

FIG. 23 is a diagram schematically illustrating arrangements of transmitter antennas 111 and receiver antennas 211 in a vehicle according to an exemplary embodiment of the inventive concept.

In the case where a vehicle is equipped with a user monitoring system 10 to monitor a driver of the vehicle, antennas 1111, 1112, and 1113 included in a transmitter 100 and antennas 2111, 2112, and 2113 included in a receiver 210 may be arranged on a straight line passing through a heart of the driver to transmit and receive pulse signals.

For example, as illustrated in FIG. 23, the transmitter antennas 111 may be mounted at a steering wheel 410 of the vehicle, and the receiver antennas 211 may be mounted at a backrest 420 of a driver's seat.

Since a driver maintains a fixed posture in which a chest of the driver faces the steering wheel 410 after sitting in the driver's seat, the transmitter antennas 111 and the receiver antennas 211 may be arranged to face each other with a measuring part (e.g., a heart) interposed therebetween. Accordingly, a pulse signal may pass through the measuring part.

Figure 24:
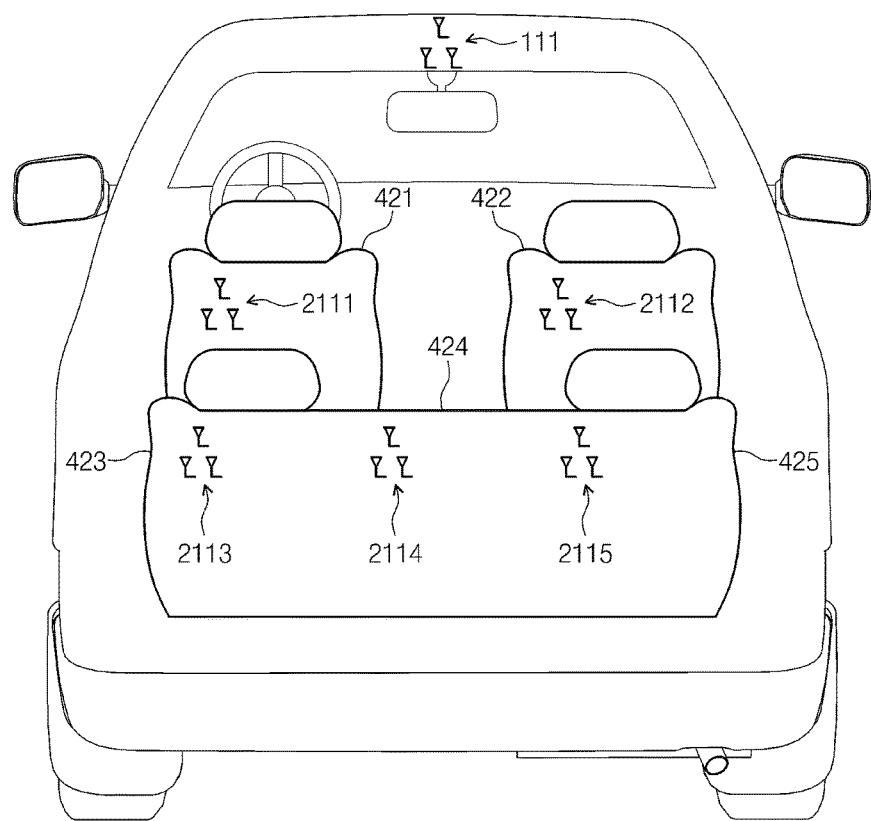
FIG. 24 is a diagram schematically illustrating a state where transmitter antennas and receiver antennas are disposed in a vehicle, according to another exemplary embodiment of the inventive concept.

FIG. 24 is a diagram schematically illustrating a state where transmitter antennas 111 and receiver antennas 2111 to 2115 are disposed in a vehicle, according to another exemplary embodiment of the inventive concept.

According to another exemplary embodiment of the inventive concept, a user monitoring system 10 may monitor passengers as well as a driver. In this case, the user monitoring system 10 may include a transmitter 100 and a receiver 210 provided every passenger to measure bio signals of the passengers. In exemplary embodiments, it may be possible to measure bio signals of passengers using one transmitter 100.

For example, as illustrated in FIG. 24, transmitter antennas 111 may be mounted at a front, top side of the interior of a vehicle, and receiver antennas 2111 to 2115 may be mounted at backrests 421 to 424 of seats of the vehicle, respectively.

As such, in the case where the transmitter antennas 111 and the receiver antennas 2111 to 2115 are arranged in a vehicle, the transmitter antennas 111 may be disposed to face the receiver antennas 2111 to 2115 with measuring parts of all passengers interposed therebetween.

According to an exemplary embodiment of the inventive concept, a plurality of antennas 1111, 1112, and 1113 included in the transmitter 100 or a plurality of antennas 2111, 2112, and 2113 included in the receiver 219 may be located on the same plane.

Figure 25:
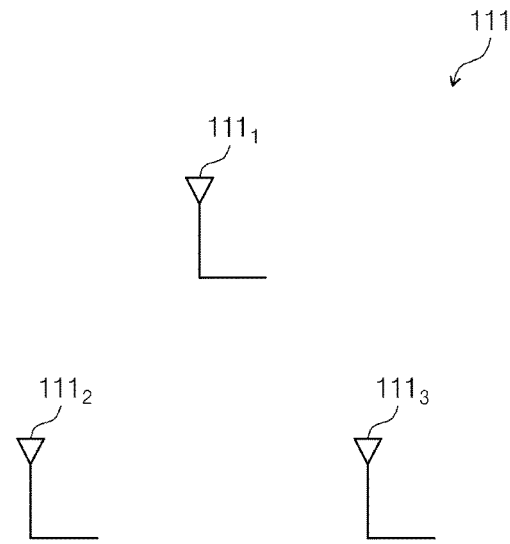
FIGS. 25 to 27 are diagrams schematically illustrating arrangement of antennas according to exemplary embodiments of the inventive concept.
Figure 26:
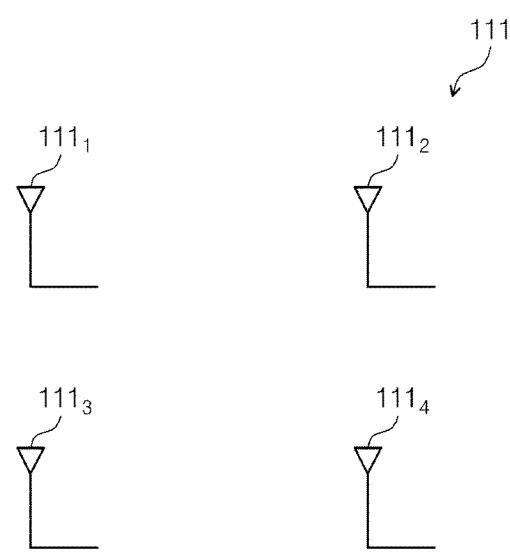
Figure 27:
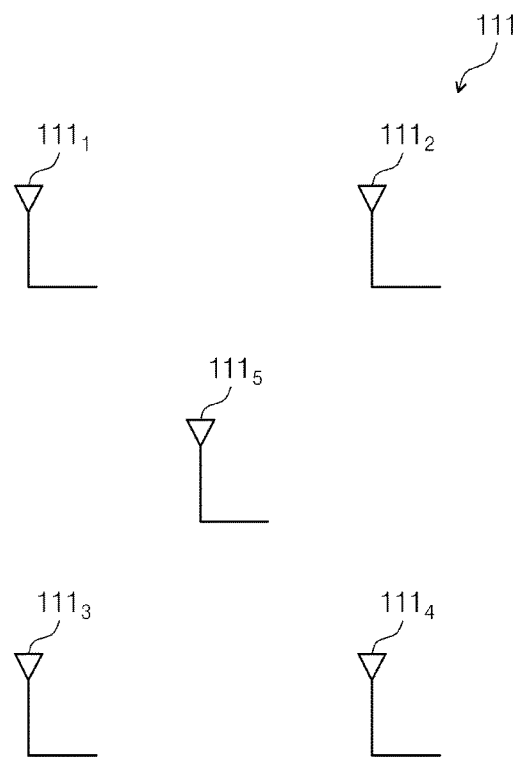

FIGS. 25 to 27 are diagrams schematically illustrating arrangement of antennas 111 according to exemplary embodiments of the inventive concept.

Antennas 111 may be located on one plane such that a polygon is formed when piecing the antennas 111 together.

For example, referring to FIG. 25, the antennas 111 may include three antennas 1111, 1112, and 1113, and the antennas 1111, 1112, and 1113 may be disposed on one plane to form a triangular shape.

As another example, referring to FIG. 26, the antennas 111 may include four antennas 1111, 1112, 1113, and 1114 and the antennas 1111, 1112, 1113, 1114 may be disposed on one plane to form a tetragonal shape.

The number of antennas included in the transmitter 100 or the number of antennas included in the receiver 210 may increase over 5 or more, not limited to 3 or 4.

Furthermore, the plurality of antennas 111 may further include an antenna, placed at the center of the polygon, as well as antennas corresponding to apexes of a polygon.

For example, referring to FIG. 27, the antennas 111 may further include an antenna 1115, placed at the center of a tetragon, as well as antennas 1111, 1112, 1113, and 1114 corresponding to apexes of the tetragon.

The above-described arrangement of antennas may be applicable to antennas included in the receiver 210 as well as antennas included in the transmitter 100. That is, even though the transmitter 100 is mounted at a point in a vehicle and receivers 210 are mounted at backrests of all seats, the transmitter 100 may transmit pulse signals toward a receiver 210 by appropriately adjusting a delay of a pulse signal to be transmitted through each antenna.

Returning to FIG. 1, a user monitoring system 10 may further include an input device 300. The input device 300 may be a device to allow a user to enter information associated with an operation of the user monitoring system 10 and may include, for example, a touch screen, a keypad, and the like.

According to an exemplary embodiment of the inventive concept, the input device 300 may input information associated with a seat where a passenger (or a person to be measured) of a vehicle sits. In this case, a transmitter 100 may transmit pulse signals toward receiver antennas mounted at a backrest of the seat where the passenger sits.

For example, in the case where persons sit at a driver's seat and a rear, right seat of five seats illustrated in FIG. 24, the input device 300 may receive an input for selecting the driver's seat and the rear, right seat as seats where persons to be measured sit, from a user (e.g., a driver).

Accordingly, the transmitter 100 may not transmit pulse signals to all receiver antennas 2111 to 2115 mounted at a vehicle, but it may transmit the pulse signals to backrests 421 and 425 of seats selected according to the input, thereby preventing unnecessary transmission and reception and processing of pulse signals.

An embodiment of the inventive concept is exemplified as the input device 300 receives information associated with a seat where a to-be-measured person sits, from a user. In some embodiments, the input device 300 may receive whether a to-be-measured person boards, from sensors respectively mounted at seats.

For example, sensors may be mounted at seat belt buckles of all seats. In the case where a seat belt is joined with the buckle, a sensor mounted at the buckle may notify the input device 300 that a to-be-measured person sits in a seat corresponding to the buckle.

According to an exemplary embodiment of the inventive concept, in the case where a seat where a to-be-measured person sits is in plurality, the transmitter 100 may transmit pulse signals toward a plurality of antennas 2111 and 2115 mounted at backrests of the seats corresponding to persons to be measured, in a time division method. That is, the transmitter 100 may transmit pulse signals to a plurality of antennas 2111 and 2115 at different times.

In the case where the user monitoring system measures a heartbeat of a to-be-measured person, a heartbeat period may generally be hundreds milliseconds or several seconds. For this reason, if an impulse corresponding to a nanosecond unit is used to measure a heartbeat, time slots may be allotted by the number of passengers to measure heartbeats of persons to be measured.

According to another exemplary embodiment of the inventive concept, the user monitoring system 10 may adjust a transmission direction of a pulse signal according to a physique of a person to be measured.

Figure 28:
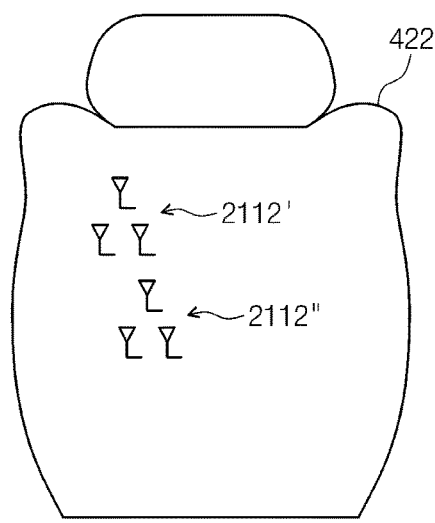
FIG. 28 is a diagram schematically illustrating arrangement of receiver antennas in a vehicle, according to still another exemplary embodiment of the inventive concept.

FIG. 28 is a diagram schematically illustrating arrangement of receiver antennas 2112' and 2112" in a vehicle, according to still another exemplary embodiment of the inventive concept.

As illustrated in FIG. 28, according to still another exemplary embodiment of the inventive concept, a receiver 210 may include a first antenna group 2112' mounted at a first portion of a backrest 422 of a seat and a second antenna group 2112" mounted at a second portion of the backrest 422.

An input device 300 may receive information associated with a physique of a to-be-measured person that boards a vehicle. A transmitter 100 may transmit pulse signals toward an antenna group, corresponding to the physique of the -be-measured person, from among the first and second antenna groups 2112' and 2112".

For example, the first antenna group 2112' formed of a plurality of antennas may be mounted at a portion, corresponding to a heart of an adult, of a backrest 422, and the second antenna group 2112" formed of a plurality of antennas may be mounted at a portion, corresponding to a heart of a child, of the backrest 422.

In the case where a user (e.g., a driver) inputs, through an input device 300, information atomic sequencer a physique of a to-be-measured person, for example, information corresponding to a child with respect to seats where the to-be-measured person sits, the transmitter 100 may transmit pulse signals toward the second antenna group 2112" being an antenna group corresponding to a child, based on the input information.

In exemplary embodiments, a physique of a person to be measured may be classified as an adult or a child, as an age, as sex, or as stature. That is, as information associated with a physique of a person to be measured, a user may not select one of an adult and a child, but may select one of male or female or input an age or stature of the person to be measured.

According to exemplary embodiments of the inventive concept, a bio signal may be measured using a pulse signal transmitted through a straight line path passing through a measuring part of a to-be-measured person, and interference due to reflected signals transmitted through a multi-path may be excluded. Accordingly, it may be possible to improve accuracy of measurement.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A bio signal measuring apparatus comprising:
a processor configured to sample a portion of a pulse included in a pulse signal penetrating a person to be measured, wherein the sampling circuitry samples portions, being different from each other, sampled from a plurality of pulses included in the pulse signal being different from each other; and
to process a sampled signal and measure a bio signal of the person to be measured based on at least one of a center frequency, a bandwidth, or amplitude of a reconstruction pulse obtained through the sampling,
wherein the processor measures a heartbeat of the person to be measured, based on at least one of a center frequency, a bandwidth, or amplitude of the reconstruction pulse, and
wherein the processor calculates a variation in at least one of a center frequency, a bandwidth, or amplitude of the reconstruction pulse and measures the heartbeat by detecting contraction and distension of a heart according to the variation.

2. The bio signal measuring apparatus of claim 1, further comprising an antenna configured to receive the pulse signal penetrating the person to be measured and provide the pulse signal to the sampling unit.

3. The bio signal measuring apparatus of claim 1, further comprising an analog-to-digital converter configured to convert a sampled signal into a digital signal and provide the digital signal to the processing unit.

4. The bio signal measuring apparatus of claim 1, wherein the pulse signal is a signal where the pulse is repeated every predetermined pulse repetition period.

5. The bio signal measuring apparatus of claim 4, wherein the processor samples the pulse in at least one time of the duration of the pulse, and wherein sampling about the pulse is performed every time obtained by adding a predetermined sampling interval to the pulse repetition period.

6. The bio signal measuring apparatus of claim 5, wherein the processor samples the pulse at a plurality of times of the duration of the pulse, and wherein an interval between the times in the duration of the pulse is equal to the sampling interval.

7. The bio signal measuring apparatus of claim 6, wherein the processor obtains an average of sampling values, corresponding to different points in the duration of the pulse, from among sampling values obtained by sampling the plurality of pulses and determines the average as a sampling value of a corresponding point.

8. The bio signal measuring apparatus of claim 1, wherein the duration of the reconstruction pulse is longer than that of the pulse.

9. The bio signal measuring apparatus of claim 1, wherein the processing unit calculates at least one of a center frequency, a bandwidth, or amplitude of the reconstruction pulse and measures the heartbeat by detecting contraction and distension of a heart according to at least one of the center frequency, the bandwidth, or the amplitude.

* * * * *